US012807661B2

(12) United States Patent
Lv et al.

(10) Patent No.: US 12,807,661 B2
(45) **Date of Patent: *Nov. 24, 2026**

(54) FUSION PROTEIN AND USE THEREOF

(71) Applicants: HANGZHOU SUMGEN BIOTECH CO., LTD., Hangzhou (CN); SUMGEN MAB (BEIJING) BIOTECH CO., LTD., Beijing (CN)

(72) Inventors: Ming Lv, Hangzhou (CN); Xiaoran Ding, Hangzhou (CN); Shiwei Miao, Hangzhou (CN); Bin Tan, Hangzhou (CN); Xuegong Wang, Hangzhou (CN)

(73) Assignees: HANGZHOU SUMGEN BIOTECH CO., LTD., Hangzhou (CN); SUMGEN MAB (BEIJING) BIOTECH CO., LTD., Beijing (CN)

( * ) Notice: Subject to any disclaimer, the term of this patent is extended or adjusted under 35 U.S.C. 154(b) by 1015 days.

This patent is subject to a terminal disclaimer.

(21) Appl. No.: 17/599,733

(22) PCT Filed: Apr. 1, 2020

(86) PCT No.: PCT/CN2020/082861

§ 371 (c)(1),
(2) Date: Sep. 29, 2021

(87) PCT Pub. No.: WO2020/200256

PCT Pub. Date: Oct. 8, 2020

(65) Prior Publication Data

US 2022/0251154 A1 Aug. 11, 2022

(30) Foreign Application Priority Data

Apr. 2, 2019 (CN) ........................ 201910260447.5

(51) Int. Cl.
*C07K 14/47* (2006.01)
*A61P 35/02* (2006.01)
(Continued)

(52) U.S. Cl.
CPC .......... *C07K 14/4703* (2013.01); *A61P 35/02* (2018.01); *C07K 14/70596* (2013.01);
(Continued)

(58) Field of Classification Search
None
See application file for complete search history.

(56) References Cited

U.S. PATENT DOCUMENTS 11,891,423 B2 * 2/2024 Lv .................... C07K 14/70596
12,304,967 B2 * 5/2025 Lv ........................... A61P 35/00
(Continued)

FOREIGN PATENT DOCUMENTS

CN 103608684 * 2/2014
CN 103608684 A 2/2014
(Continued)

OTHER PUBLICATIONS

Lee et al., Sci Rep 7, 5532 (2017) (Year: 2017).*
(Continued)

*Primary Examiner* — Karl J Puttlitz
(74) *Attorney, Agent, or Firm* — Sughrue Mion, PLLC

(57) ABSTRACT

Provided are a fusion protein, and an immunoconjugate, a nucleic acid molecule, a carrier, a composition, a cell and a preparation method related thereto, for treating tumors and/or autoimmune diseases.

16 Claims, 5 Drawing Sheets

Specification includes a Sequence Listing.

(51) Int. Cl.
*C07K 14/705* (2006.01)
*C12N 15/62* (2006.01)

(52) U.S. Cl.
CPC .......... *C12N 15/62* (2013.01); *C07K 2317/73* (2013.01); *C07K 2319/21* (2013.01)

(56) References Cited

U.S. PATENT DOCUMENTS

| | | | | | |
|---|---|---|---|---|---|
| 2021/0171593 | A1* | 6/2021 | Lv | ........................... | A61P 29/00 |
| 2021/0317230 | A1* | 10/2021 | Lv | .................... | C07K 14/70503 |

FOREIGN PATENT DOCUMENTS

| | | | | | |
|---|---|---|---|---|---|
| CN | 107459578 | A | | 12/2014 | |
| CN | 107459578 | | * | 5/2016 | |
| CN | 109535263 | | * | 12/2018 | |
| CN | 109535263 | A | | 3/2019 | |
| WO | 2016024021 | A1 | | 2/2016 | |
| WO | 2018205936 | A1 | | 11/2018 | |
| WO | WO-2019201236 | A1 | * | 10/2019 | .............. A61P 19/02 |
| WO | WO-2020098672 | A1 | * | 5/2020 | ....... C07K 14/70596 |

OTHER PUBLICATIONS

Machine Translation of CN 103608684 at https://patents.google.com/patent/CN103608684B/en?oq=103608684+ downloaded Mar. 14, 2025 (Year: 2014).*

Machine Translation of CN 109535263 at https://patents.google.com/patent/CN109535263A/en?oq=109535263+ downloaded Mar. 14, 2025 (Year: 2022).*

Machine Translation of CN 107459578 at https://patents.google.com/patent/CN107459578B/en?oq=107459578+ downloaded Mar. 14, 2025 (Year: 2017).*

Liu et al., mAbs, 10(2), 315-324 (Year: 2018).*

Liu, B., et al., Elimination of tumor by CD47/PD-L1 dual-targeting fusion protein that engages innate and adaptive immune responses, MABS, vol. 10, No. 2, pp. 315-324, Taylor & Francis Group, LLC, 2018.

Weiskopf, K., et al., Engineered SIRPa variants as immunotherapeutic adjuvants to anti-cancer antibodies, Science, 341(6141), Jul. 5, 2013.

PCT/CN2020/082861 International Search Report dated Jun. 23, 2020.

Lee, H.T., et al., Molecular mechanism of PD-1/PD-L1 blockad via anti-PD-L1 antibodies atezolizumab and durvalumab, Scientific Reports, Jul. 17, 2017.

* cited by examiner

FUSION PROTEIN AND USE THEREOF

CROSS-REFERENCE TO RELATED APPLICATIONS

This application is a National Stage Application and claims priority under 35 U.S.C. § 371 to Patent Cooperation Treaty application PCT/CN2020/082861, filed Apr. 1, 2020, which claims the benefit of CN 201910260447.5 filed Apr. 2, 2019. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2021-09-23_Sequence-Listing_ST25" is 67,464 bytes in size and was created on Sep. 23, 2021, and filed electronically herewith.

FIELD OF THE INVENTION

The present application relates to the field of biomedicine, and particularly to a multispecific fusion protein, and further to a use thereof in the treatment of a tumor and/or an autoimmune disease.

BACKGROUND OF THE INVENTION

At present, in the field of tumor therapy, there are two major methods of administering targeted drugs and immunotherapy. There may be an interaction between these two therapies, causing a stronger cytotoxic effect, thus alleviating the tumors steadily and sustainably. However, the interaction between targeted drugs and immunotherapy is very complicated, and the overall antitumor effect and the toxicity profile of the combined therapy may be affected by various factors such as species, dosages, order, dosage forms and the like.

Programmed death 1 (PD-1) antibody is an immunotherapy. PD-1 is expressed in activated T cells, B cells and myeloid cells, which has two ligands, i.e., programmed death ligand 1 (PD-L1) and PD-L2. PD-1 and/or PD-L1 inhibitors can specifically bind to PD-L1 on tumor cells to achieve an anti-tumor effect, but the clinical response rate is low, and there may be some side effects, e.g., causing pneumonia, colitis, hepatitis, etc.

CD47 protein is a kind of transmembrane glycoprotein, which is a member belonging to the immunoglobulin superfamily. In addition to being expressed by normal tissue cells, CD47 is over-expressed by many tumor cells. CD47 on the surface of tumors cells binds to SIRPα on the surface of macrophages, which prevents the phagocytosis of tumor cells by macrophages, this is considered as one mechanism by which tumors evade from the surveillance of an immune system. Blocking the interaction between CD47 protein and SIRPα can inhibit the tumor growth.

However, the current reagents used to block the interaction between CD47 protein and SIRPα have limited recognition activity, their affinities with CD47 protein are always insufficient, so they have limited capacity on inhibiting the tumors. In addition, the current antibody drugs targeting CD47 may cause side effects such as anemia responses or thrombocytopenia. Therefore, it is urgent to obtain an effective therapy which specifically targets both CD47 protein and associated tumor antigens.

SUMMARY OF THE INVENTION

The present application provides a fusion protein, including a first binding domain that specifically binds PD-L1 and a second binding domain that specifically binds a CD47 protein. The present application also provides an immunoconjugate including the fusion protein; a nucleic acid molecule encoding the fusion protein; a vector, a composition and a cell capable of including and/or expressing the fusion protein; and a method of preparing the fusion protein. The fusion protein, the immunoconjugate, the nucleic acid molecule, the vector, the composition and the cell of the present application have one or more of the following properties: 1) capable of specifically binding the CD47 protein and PD-L1 simultaneously; 2) capable of specifically blocking the interaction between the CD47 protein and SIRPα; 3) capable of specifically blocking the interaction between PD-1 and PD-L1; 4) capable of effectively inhibiting the growth and/or proliferation of tumors or tumor cells.

In one aspect, the present application provides a fusion protein, including a first binding domain that specifically binds PD-L1; and a second binding domain that specifically binds a CD47 protein; wherein, the second binding domain comprises a mutant of a human SIRPα variant 1, the mutant comprises substitution, deletion or addition of an amino acid residue at one or more positions from site 33 to site 149 compared to the sequence as shown in SEQ ID NO: 29.

In some embodiments, the mutant comprises amino acid substitutions at one or more amino acid residues selected from the group consisting of: I61, V63, E77, Q82, K83, E84, V93, D95, L96, K98, N100, R107, G109 and V132.

In some embodiments, the mutant comprises amino acid substitutions at amino acid residues selected from the group consisting of: (1) I61, V63, E77, E84, V93, L96, K98, N100 and V132; (2) 161, E77, Q82, K83 and E84; (3) I61, V63, K83, E84 and V132; (4) I61, E77, E84, R107 and V132; (5) I61, V63, E77, K83, E84 and N100; (6) I61, E77, Q82, K83, E84 and R107; (7) I61, E77, Q82, E84, V93, L96, N100, R107, G109 and V132; (8) I61, E77, Q82, K83, E84 and V132; (9) I61; (10) 161, D95, L96, G109 and V132; (11) I61, D95, L96, K98, G109 and V132; (12) I61, E77, E84, V93, R107 and V132; (13) E77, L96, N100, G109 and V132; (14) I61, V63, Q82, E84, D95, L96, N100 and V132; (15) I61, E77, Q82, K83, E84, V93, D95, L96, K98, N100 and V132; (16) I61, E77, Q82, K83, E84 and V93; (17) I61, V63, E77, K83, E84, D95, L96, K98 and N100; (18) I61, V63, E77, K83, D95, L96, K98, N100 and G109; (19) I61, E77, Q82, E84, V93, D95, L96, K98 and N100; and (20) 161, V63, E77, Q82 and E84.

In some embodiments, the mutant comprises one or more amino acid substitutions selected from the group consisting of: 161L/V/F, V63I, E77I/N/Q/K/H/M/R/N/V/L, Q82S/R/G/N, K83R, E84K/H/D/R/G, V93L/A, D95H/R/E, L96S/T, K98R, N100G/K/D/E, R107N/S, G109R/H and V132L/R/I/S.

In some embodiments, the mutant comprises amino acid substitutions selected from the group consisting of: (1) I61L, V63I, E77I, E84K, V93L, L96S, K98R, N100G and V132L; (2) I61V, E77N, Q82S, K83R and E84H; (3) I61F, V63I, K83R, E84K and V132I; (4) I61L, E77Q, E84D, R107N and V132I; (5) I61L, V63I, E77K, K83R, E84D and N100G; (6) I61V, E77H, Q82R, K83R, E84H and R107S; (7) I61L, E77I, Q82G, E84R, V93L, L96T, N100G, R107S, G109R and V132R; (8) I61L, E77M, Q82G, K83R, E84D and V132L; (9) I61L; (10) I61F, D95H, L96S, G109H and V132S; (11) I61F, D95H, L96S, K98R, G109H and V132S; (12) I61L, E77Q, E84D, V93A, R107N and V132I; (13) E77K, L96S, N100K, G109H and V132L; (14) I61L, V63I, Q82G, E84G, D95R, L96S, N100D and V132I; (15) I61L, E77R, Q82N, K83R, E84G, V93L, D95E, L96T, K98R, N100D and V132L; (16) I61V, E77N, Q82S, K83R, E84H and V93A; (17) I61V, V63I, E77V, K83R, E84D, D95E, L96T, K98R and N100E; (18) I61L, V63I, E77V, K83R, D95E, L96S, K98R, N100D and G109R; (19) I61V, E77L, Q82G, E84G, V93L, D95E, L96T, K98R and N100G; and (20) I61L, V63I, E77N, Q82G and E84G.

In some embodiments, the mutant comprises an amino acid sequence as shown in any one of SEQ ID NOs: 30-49.

In some embodiments, the first binding domain comprises an antibody or an antigen-binding fragment or a variant thereof. In some embodiments, the antibody is selected from the group consisting of: a monoclonal antibody, a single-chain antibody, a chimeric antibody, a humanized antibody and a fully human antibody. In some embodiments, the antigen-binding fragment is selected from the group consisting of: Fab, Fab', F(ab')2, F(ab)2, dAb, an isolated complementary determining region CDR, Fv and scFv.

In some embodiments, the PD-L1 is a human PD-L1.

In some embodiments, the antibody comprises a heavy chain of the antibody or a fragment thereof, the heavy chain of the antibody or the fragment thereof comprises HCDR1-3, and the HCDR1 comprises an amino acid sequence as shown in any one of the group consisting of: SEQ ID NO: 4 and SEQ ID NO: 18. In some embodiments, the HCDR2 comprises an amino acid sequence as shown in any one of the group consisting of: SEQ ID NO: 5 and SEQ ID NO: 19. In some embodiments, the HCDR3 comprises an amino acid sequence as shown in any one of the group consisting of: SEQ ID NO: 6 and SEQ ID NO: 20. In some embodiments, the heavy chain of the antibody or the fragment thereof comprises a heavy chain variable region VH, and the heavy chain variable region VH comprises an amino acid sequence as shown in any one of the group consisting of: SEQ ID NO: 8 and SEQ ID NO: 22. In some embodiments, the heavy chain of the antibody or the fragment thereof comprises a heavy chain constant region, and the heavy chain constant region comprises IgG. In some embodiments, the IgG is selected from the group consisting of: IgG1 and IgG4. In some embodiments, the heavy chain of the antibody comprises an amino acid sequence as shown in any one of the group consisting of: SEQ ID NO: 13 and SEQ ID NO: 27.

In some embodiments, the antibody comprises a light chain of the antibody or a fragment thereof, the light chain of the antibody or the fragment thereof comprises LCDR1-3, the LCDR1 comprises an amino acid sequence as shown in any one of the group consisting of: SEQ ID NO: 1 and SEQ ID NO: 15. In some embodiments, the LCDR2 comprises an amino acid sequence as shown in any one of the group consisting of: SEQ ID NO: 2 and SEQ ID NO: 16. In some embodiments, the LCDR3 comprises an amino acid sequence as shown in any one of the group consisting of: SEQ ID NO: 3 and SEQ ID NO: 17. In some embodiments, the light chain of the antibody or the fragment thereof comprises a light chain variable region VL, and the light chain variable region VL comprises an amino acid sequence as shown in any one of the group consisting of: SEQ ID NO: 7 and SEQ ID NO: 21. In some embodiments, the light chain of the antibody or the fragment thereof comprises a light chain constant region, and the light chain constant region comprises Igκ. In some embodiments, the light chain of the antibody comprises an amino acid sequence as shown in any one of the group consisting of: SEQ ID NO: 11 and SEQ ID NO: 25.

In some embodiments, the first binding domain is located at N-terminal of the second binding domain. In some embodiments, the fusion protein further comprises a linker, the linker is located at C-terminal of the first binding domain and located at N-terminal of the second binding domain. In some embodiments, the linker comprises an amino acid sequence as shown in SEQ ID NO: 52.

In some embodiments, the fusion protein comprises at least two of the second binding domains. In some embodiments, each of the second binding domains is located at C-terminal of the first binding domain respectively.

In another aspect, the present application provides an immunoconjugate, which comprises the fusion protein.

In another aspect, the present application provides one or more isolated nucleic acid molecules, which encode the fusion protein or the immunoconjugate.

In another aspect, the present application provides one or more vectors, which comprise the nucleic acid molecules.

In another aspect, the present application provides a composition, which comprises the fusion protein, the immunoconjugate, or the nucleic acid molecule, and optionally, pharmaceutically acceptable excipients.

In another aspect, the present application provides a cell, which comprises the fusion protein, the immunoconjugate, the nucleic acid molecule, or the vector.

In another aspect, the present application provides a method of preparing the fusion protein, which comprises culturing the cell under a condition enabling the expression of the fusion protein.

In another aspect, the present application provides a use of the fusion protein, the immunoconjugate, the nucleic acid molecule, the vector, the composition, or the cell in the preparation of a medicament, wherein the medicament is used for treating a tumor.

In some embodiments, the tumor comprises a solid tumor and a non-solid tumor.

In some embodiments, the solid tumor and the non-solid tumor comprise multiple myeloma, leukemia, Non-Hodgkin's lymphoma, Hodgkin's lymphoma, neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer, frontal sinus tumor, hypopharyngeal cancer, olfactory neuroblastoma, tongue cancer, gingival carcinoma, ampulla carcinoma, colon cancer, rectal cancer, kidney cancer, ureteral carcinoma, bladder cancer, penile cancer, fallopian tube carcinoma, eyelid cancer, retinoblastoma.

In another aspect, the present application provides the fusion protein, the immunoconjugate, the nucleic acid molecule, the vector, the composition, or the cell, which are used for treating a tumor.

In another aspect, the present application provides a method of blocking the interaction between the PD-L1 protein and PD-1, comprising administering to a subject in need thereof an effective amount of the fusion protein, the immunoconjugate, the nucleic acid molecule, the vector, the composition, or the cell.

In another aspect, the present application provides a method of blocking the interaction between the CD47 protein and SIRPα, comprising administering to a subject in need thereof an effective amount of the fusion protein, the immunoconjugate, the nucleic acid molecule, the vector, the composition, or the cell.

In another aspect, the present application provides a method of inhibiting the growth and/or proliferation of tumors o tumor cells, comprising administering to a subject in need thereof an effective amount of the fusion protein, the immunoconjugate, the nucleic acid molecule, the vector, the composition, or the cell.

In another aspect, the present application provides a method of preventing or treating tumors in a subject, comprising administering to the subject in need thereof an effective amount of the fusion protein, the immunoconjugate, the nucleic acid molecule, the vector, the composition, or the cell.

In another aspect, the present application provides the fusion protein, the immunoconjugate, the nucleic acid molecule, the vector, the composition, or the cell, which are used for preventing or treating tumors in a subject.

Other aspects and advantages of the present application can be conceived easily by those skilled in the art from the following detailed description. The following detailed description only shows and describes exemplary embodiments of the present application. As will be recognized by those skilled in the art, the content of the present application enables those skilled in the art to make changes to the disclosed specific embodiments without departing from the spirit and scope of the invention to which the present application is related. Correspondingly, the attached drawings of the present application and the description of the specification are only exemplary, but not restrictive.

BRIEF DESCRIPTION OF THE DRAWING

The specific features related to the present application are shown in the accompanying claims. The characteristics and advantages related to the present application will be better understood with reference to the exemplary embodiments and the attached drawings described in detail below. The attached drawings are illustrated briefly as below:

DETAILED DESCRIPTION

Figure 1:
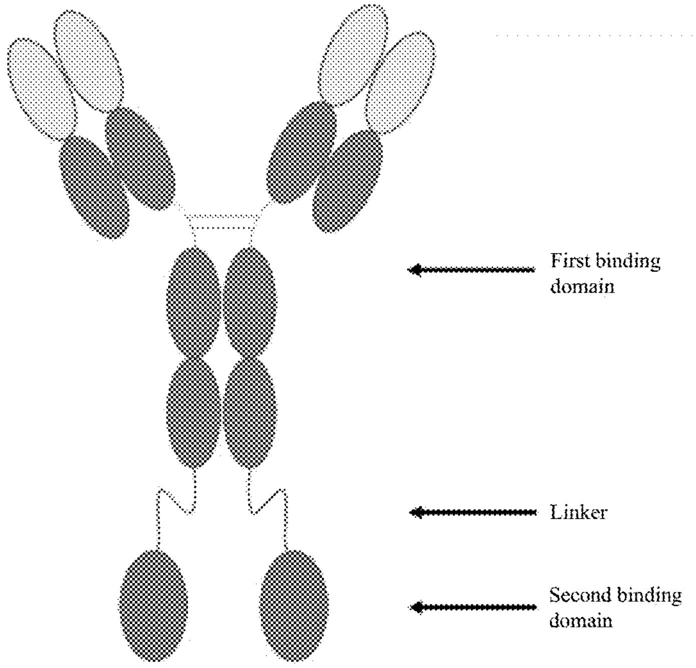
FIG. 1 shows an exemplary structure of the fusion protein according to the present application.

The implementation of the present application will be illustrated in the following specific embodiments, and other advantages and effects of the present application will be easily known by persons familiar with the technology from the disclosures in the specification.

In the present application, the term "fusion protein" generally refers to a protein obtained from the fusion of two or more proteins or polypeptides. The fusion protein can be prepared artificially through a recombinant DNA technology. For example, the genes or nucleic acid molecules encoding the two or more proteins or polypeptides can be linked with each other to form a fusion gene or a fused nucleic acid molecule, which can encode the fusion protein. The translation of the fusion genes can produce a single polypeptide, which can possess the properties of at least one, or even each of the two or more proteins or polypeptides before fusion.

In the present invention, the term "specifically binds" generally refers to the non-random binding reaction between two molecules, such as the reaction between an antibody and an antigen producing the antibody. One antibody specific to a certain antigen means binding to the antigen with an affinity (KD)<$10^{-5}$ M (e.g., $10^{-6}$ M, $10^{-7}$ M, $10^{-8}$ M, $10^{-9}$ M, $10^{-10}$ M, etc.), wherein KD refers to the ratio of dissociation rate to binding rate ($k_{off}/k_{on}$), which can be determined by a method familiar to technicians in the field.

In the present application, the term "binding domain" generally means a domain that can specifically bind and/or recognize a specific epitope on a target (e.g., an antigen). In the present application, the term "domain" generally refers to a closely spherical structural region that is clearly separated in the subunit structure of a protein. For example, a polypeptide chain firstly can be a regular secondary structure formed from adjacent amino acid residues in some regions, then adjacent secondary structural fragments can be assembled together to form a super-secondary structure; on such a basis, the polypeptide chain can be folded into a tertiary structure that is almost spherical. For larger protein molecules or subunits, the polypeptide chain often may be a tertiary structure that is formed by the association of two or more relatively independent regional structures which can be clearly distinguished in space, and such a relatively independent regional structure can be referred as a domain.

In the present application, "the first", "the second" as used in the terms "the first binding domain" and "the second binding domain" are only used for distinction in description.

In the present application, the term "CD47 protein" generally refers to an integrin-associated protein (TAP), which is a multiple transmembrane receptor belonging to the immunoglobulin superfamily. For example, CD47 protein can bind to membrane integrins, and also bind to their ligands thrombospondin-1 (TSP-1) and signal-regulatory protein alpha (SIRPα). CD47 protein is widely expressed on the surface of cell membrane. In the present application, the CD47 protein may comprise any variants, isotypes and species homologues of a human CD47. The amino acid sequence of the human CD47 protein is listed as CEJ95640.1 in the GenBank. The CD47 protein can be expressed naturally by cells or expressed on cells transfected with CD47 genes.

In the present application, the term "SIRPα" generally refers to a regulatory membrane glycoprotein from the SIRP family, which can be used as the ligand of CD47 protein. In the present application, the SIRPα may comprise human SIRPα, for example, SIRPα variant 1 and SIRPα variant 2. The SIRPα variant 2 is different from the SIRPα variant 1 in 13 amino acids, and its amino acid sequence is listed as CAA71403.1 in GenBank. In the present application, the term "SIRPα variant 1" generally refers to a SIRPα protein of which the amino acid sequence is listed as NCBI RefSeq NP 542970.1 (residues 31-504 constitute a mature type), then the amino acid sequence of the SIRPα variant 1 is shown in SEQ ID NO: 29.

The term "antibody" generally refers to a protein comprising one or more polypeptides essentially encoded by immunoglobulin genes or immunoglobulin gene fragments. For example, immunoglobulin genes may comprise κ, λ, α, γ, δ, ε and μ constant region genes, as well as numerous variable region genes of immunoglobulin. For example, the light chain can be classified into κ or λ, which can define the types of immunoglobulin respectively: Igκ and Igλ. The heavy chain can be classified into γ, μ, α, δ or ε, which, in turn, define the types of immunoglobulin respectively: IgG, IgM, IgA, IgD and IgE. For example, the antibody may have structural units comprising tetramers, each of the tetramers can be composed of two pairs of the same polypeptide chains, and each pair has a "light chain" (about 25 kD) and a "heavy chain" (about 50-70 kD), the N-terminal of each member can define a variable region of about 100 to 110 or more amino acids, which is mainly responsible for the recognization of antigens. For example, the terms "light chain variable region (VL)" and "heavy chain variable region (VH)" generally refer to the variable region of a light chain and a heavy chain respectively. The antibody may exist as a complete immunoglobulin or as many fully characterized fragments produced by digestion with various peptidases or de novo expression.

In the present invention, the term "antigen-binding fragment" generally refers to one or more parts of a full-length antibody, in which the parts substantially maintain the capacity of binding the same antigen (e.g., PD-L1) that the antibody binds, and they can compete with the full-length antibody for specifically binding to the antigen. In general, see Fundamental Immunology, Ch. 7 (Paul, W., ed., Edition 2, Raven Press, N.Y. (1989), the entire contents of which are incorporated herein by reference. Antigen-binding fragments can be produced by a recombinant DNA technology or through the enzymatic or chemical cleavage of a complete antibody. In some cases, the antigen-binding fragments comprise Fab, Fab', F(ab')2, (Fab)2, Fd, Fv, dAb and complementary determining region (CDR) fragments, a single-chain antibody (e.g., scFv), a chimeric antibody, a diabody and a polypeptide that comprises at least a portion of an antibody sufficient to confer specific antigen binding capacity to the polypeptide. Conventional technologies known to technicians in the field (e.g., a recombinant DNA technology or an enzymatic or chemical cleavage process) can be used to obtain the antigen-binding fragments of an antibody from a given antibody, and screen the antigen-binding fragments of the antibody in terms of specificity in the same way as for complete antibodies. For example, pepsin can digest the antibodies in the hinge region below the disulfide bond so as to produce F(ab')2.

In the present application, the term "Fab" generally refers to antibody fragments composed of VL, VH, CL and CH1 domains.

In the present application, the term "Fab'" generally refers to antibody fragments with several additional residues at the carboxyl terminal of CH1 domain compared to Fab fragments. For example, Fab' may comprise one or more cysteine coming from the hinge region of the antibody.

In the present application, the term "F(ab)2" generally refers to antigen-binding fragments obtained from paired Fab fragments linked with cysteine.

In the present application, the term "dAb fragments" generally refers to antibody fragments composed of VH domains (Ward et al, Nature 341:544-546 (1989)).

In the present application, the term "complementary determining regions CDR" generally refers to the 3 hypervariable regions (HVRs) of the light chain variable region (VL) and the heavy chain variable region (VH), and the hypervariable regions are also known as complementary determining regions because these regions may form precise spatial complementarity with antigenic determinants.

In the present application, the term "Fv fragments" generally refers to antibody fragments composed of single-armed VL and VH domains of the antibody.

In the present application, the term "scFv" generally refers to a molecule composed of the heavy chain variable region and the light chain variable region of the antibody linked by a short peptide linker, which is also known as a single-chain antibody.

In the present application, the term "monoclonal antibody" generally refers to a group of antibodies which are substantially homologous, and various antibodies contained in this group may be identical except for the possible presence of naturally occurring mutations in trace amounts. The monoclonal antibodies are highly specific, directly with respect to a single antigenic site. In addition, as opposed to a polyclonal antibody preparation that comprises different antibodies with respect to different determinants (epitopes), the modifier "monoclonal" of each monoclonal antibody with respect to the single determinant on the antigen is not interpreted as requiring the production of antibodies by any particular methods. For example, monoclonal antibodies may be prepared by a hybridoma technique or monoclonal antibodies may be produced in bacterial, eukaryotic animal or plant cells by a recombinant DNA process, and can also be obtained from a phage antibody library, for example, using the technology described in Clackson et al., Nature, 352:624-628(1991) and Marks et al., Mol. Biol., 222:581-597 (1991).

In the present application, the term "chimeric antibody" generally refers to such an antibody, wherein a part of each heavy chain or light chain amino acid sequence is homologous to a corresponding amino acid sequence in an antibody from a particular species, or belongs to a particular category, and the remaining segments of the chain are homologous to the corresponding sequences of another species. For example, the variable regions of the light chain and the heavy chain are derived from the variable regions of an antibody in one animal species (e.g., mice, rats, etc.), while the constant part is homologous to the sequence of an antibody from another species (e.g., human). For example, to obtain chimeric antibodies, non-human B cells or hybridoma cells can be utilized to produce variable regions, and the constant regions combined with them are derived from human. The variable regions have the advantage of easy preparation, and their specificity is not affected by the source of the constant regions combined with them. Meanwhile, because the constant regions of chimeric antibodies may be derived from human, so chimeric antibodies are less likely to elicit an immune response at the time of injection than using antibodies with non-human derived constant regions.

In the present application, the term "humanized antibody" generally refers to a modified antibody which reduces the immunogenicity of an antibody, an immunoglobulin binding protein and a polypeptide derived from non-human species (e.g., mice or rats) to humans, and still retain the antigen-binding properties of the original antibody. For example, the humanized antibody can be prepared by the genetic engineering technology, and non-human binding domains can be humanized using CDR grafting (Jones et al., Nature 321:522

(1986)) and the variant thereof by technical means including reshaping (Verhoeyen, et al., 1988 Science 239:1534-1536; Riechmann, et al., 1988 Nature 332:323-337; Tempest, et al., Bio/Technol 1991 9:266-271), hyperchimerization (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154) and veneering (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If other regions, for example, the hinge region and the constant region domains, are also derived from non-human sources, these regions may also be humanized.

In the present application, the term "fully human antibody" generally refers to an antibody obtained by expressing genes encoding human antibody in genetically engineered animal with antibody gene deletion. For example, by means of a transgenic or trans-chromosomal technology, all the genes that encode human antibody can be transferred into genetically engineered animal with antibody gene deletion so that the animal can express the human antibody.

The protein, polypeptide and/or amino acid sequence referred in the present application should also be further understood to comprise the following range: variants or homologs having the same or similar functions as the protein or polypeptide.

In the present application, the variant may be a protein or a polypeptide with substitution, deletion or addition of one or more amino acids in the amino acid sequence of the protein and/or the polypeptide (e.g., an antibody or an fragment thereof that specifically binds the PD-L1 protein). For example, the functional variant may comprise a protein or a polypeptide with amino acid modifications by at least one, for example 1-30, 1-20 or 1-10, further for example 1, 2, 3, 4 or 5 amino acid substitution, deletion and/or insertion. The functional variant can essentially maintain the biological characteristics of the protein or the polypeptide before modification (e.g., substitution, deletion or addition). For example, the functional variant can maintain at least 60%, 70%, 80%, 90%, or 100% of the biological characteristics of the protein or the polypeptide before modification (e.g., antigen binding capacity). For example, the substitution may be conservative substitution.

In the present application, the homolog may be a protein or a polypeptide that has at least about 85% (e.g., having at least about 85%, about 90%, about 91%, about 92%, about 93%, about 94%, about 95%, about 96%, about 97%, about 98%, about 99% or higher) of sequence homology with the amino acid sequence of the protein and/or the polypeptide (e.g., the antibody or a fragment thereof that specifically binds the PD-L1 protein).

In the present application, the homology generally refers to the comparability, similarity, or relevance between two or more sequences. The "sequence homology percentage" can be calculated by the following means: two sequences to be compared are compared in a comparison window to determine the number of positions of the same nucleic acid bases (e.g., A, T, C, G, I) or the same amino acid residues (e.g., Ala, Pro, Ser, Thr, Gly, Val, Leu, Ile, Phe, Tyr, Trp, Lys, Arg, His, Asp, Glu, Asn, Gln, Cys and Met) contained in the two sequences so as to get the number of matched positions, which is divided by the total number of positions in the comparison window (i.e., the window size), and then multiplied by 100 to get the sequence homology percentage. The comparison for determining the sequence homology percentage can be achieved through various ways known in the art, for example, using publicly available computer software such as BLAST, BLAST-2, ALIGN or Megalign (DNASTAR) software. Technicians in this field can determine parameters appropriate for aligning sequences, including any algorithms required for realizing the maximum alignment in the range of the full-length sequence being compared or in the target sequence region. The homology can also be determined by the following methods: FASTA and BLAST. The description of FASTA algorithm can be seen in Improved Tool for Comparison of Biological Sequences to W. R. Pearson and D. J. Lipman, Proc. Natl. Acad. Sci., 85: 2444-2448, 1988; and Fast and Sensitive Protein Comparability Search to D. J. Lipman and W. R. Pearson, Science, 227: 1435-1441, 1989. The description of BLAST algorithm can be seen in A Basic Search Tool for Local Alignment to S. Altschul, W. Gish, W. Miller, E. W. Myers and D. Lipman, Journal of Molecular Biology, 215: 403-410, 1990.

In the present application, the term "PD-L1" generally refers to the ligand of programmed death-1 (PD-1) protein, which is also known as CD274, B7-H or B7H1. PD-1 negatively modulates the signaling of a T cell antigen receptor by interacting with the specific ligand (PD-L). The PD-L1 may be the prognostic indicator of various tumors. In the present application, the PD-L1 may be a human PD-L1. The Gene ID of the human PD-L1 in GenBank is 29126.

In the present application, the term "PD-1" generally refers to a member in the synuclein family, which can also be known as NACP, PARK1 or PARK4. In the present application, the PD1 may be a human PD1. The Gene ID of the human PD-L1 in GenBank is 6622.

Generally, in a polypeptide chain, an amino group is linked with another carboxyl group in the polypeptide chain so as to become one chain, but at the two terminals of the protein, there remain amino acid residues that do not form peptide bonds respectively, which are a polypeptide chain terminal carrying free amino groups and a polypeptide chain terminal carrying carboxyl groups respectively. In the present application, the term "N-terminal" generally refers to the polypeptide chain terminal with an amino acid residue carrying free amino groups. In the present application, the term "C-terminal" generally refers to the polypeptide chain terminal with an amino acid residue carrying free carboxyl groups.

In the present application, the term "nucleic acid molecule" generally refers to nucleotide, deoxyribonucleotide or ribonucleotide or an analogue thereof in isolated forms of any length which is isolated from natural environment or synthesized artificially.

In the present application, the term "immunoconjugate" generally refers to a polypeptide molecule with immune function in which one or more heterogenous molecules (including, but not limited to, cytotoxin) are conjugated. In the present application, "conjugate" and "link", "fusion" can be used interchangeably in the present application, and generally refers to that two or more chemical elements, sequences or components are linked together, for example by means including chemical conjugation or recombination. The heterogenous molecule may be a cytotoxin, a chemotherapeutic agent, etc. For example, the fusion protein of the present application can be conjugated with one or more heterogenous molecules (e.g., cytotoxin) to get the immunoconjugate.

In the present invention, the term "vector" refers to a nucleic acid delivery vehicle into which a polynucleotide encoding a certain protein can be inserted so that the protein can be expressed. The vector makes the genetic material element it carries be expressed in a host cell through transforming, transducing or transfecting the host cell. For example, the vector comprises: plasmid; phagemid; cosmid; artificial chromosomes, such as yeast artificial chromosome (YAC), bacterial artificial chromosome (BAC) or P1-derived artificial chromosome (PAC); phages, such as λ phage or M13 phage; and animal viruses and the like. The variaties of animal viruses used as the vector comprise retrovirus (including lentivirus), adenovirus, adeno-associated virus, herpes virus (e.g., herpes simplex virus), poxvirus, baculovirus, papilloma virus, papovavirus (e.g., SV40). A vector may contain various elements for controlling the expression, including a promoter sequence, a transcription initiation sequence, an enhancer sequence, a selection element and a reporter gene. In addition, the vector may also contain replication origins. The vector could also comprise a component that help it get into the cell, such as a virion, a liposome or a protein coat, but not just these substances.

In the present application, the term "tumor" generally refers to neoplasms formed from the proliferation of local histocytes in the organisms of mammals (e.g., cells or parts thereof) under the action of various tumorigenic factors. In the present application, the tumor may comprise a solid tumor and a non-solid tumor. The solid tumor may comprise neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer. In the present application, the non-solid tumor may comprise multiple myeloma, leukemia, Non-Hodgkin lymphoma, Hodgkin's lymphoma.

In the present application, the term "comprise" generally means including definitely specified features, but not excluding other factors.

In the present application, the term "about" generally refers to variations in a range of 0.5%-10% above or below a specified value, for example, variations in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified value.

Fusion Protein

In one aspect, the present application provides a fusion protein, the fusion protein may comprise a first binding domain and a second binding domain. The first binding domain can specifically bind PD-L1; the second binding domain can specifically bind a CD47 protein, the second binding domain may comprise a mutant of a human SIRPα variant 1, and the mutant comprises substitution, deletion or addition of amino acid residues at one or more (e.g., 1-2, 1-3, 1-4, 1-5, 1-6, 1-7, 1-8, 1-9, 1-10 or more) positions from site 33 to site 149 compared to the sequence as shown in SEQ ID NO: 29. The fusion protein of the present application can specifically bind both tumor-associated antigen and CD47 protein, thereby playing a role in the treatment of tumors and/or autoimmune diseases.

In the present application, the term "the first binding domain" generally refers to a domain that can specifically bind PD-L1. The term "the second binding domain" generally refers to a domain that can specifically bind a CD47 protein.

The Second Binding Domain that Specifically Binds CD47

In the present application, the mutant (e.g., a mutant of a human SIRPα variant 1 that specifically binds a CD47 protein) comprises amino acid substitutions at one or more (e.g., 1-2, 1-3, 1-4, 1-5, 1-6, 1-7, 1-8, 1-9, 1-10 or more) amino acid residues selected from the group consisting of: I61, V63, E77, Q82, K83, E84, V93, D95, L96, K98, N100, R107, G109 and V132.

In the present application, the positions of amino acid residues in the amino acid substitution mean the numbers of the residues determined based on the amino acid sequence as shown in SEQ ID NO: 29.

In the present application, "amino acid substitution Xn" means that an amino acid substitution occurs at the residue X of site n in the corresponding amino acid sequence as shown in SEQ ID NO: 29, in which n is a positive integer, X is the abbreviation of any one amino acid residue. For example, "amino acid substitution 161" indicates that an amino acid substitution occurs at the residue I of site 61 in the corresponding amino acid sequence as shown in SEQ ID NO: 29.

In the present application, the amino acid substitutions may be nonconservative substitutions. The nonconservative substitutions may comprise changing amino acid residues in target proteins or polypeptides in a nonconservative form, for example, changing an amino acid residue with a certain side chain size or a certain property (e.g., hydrophilic) into another amino acid residue with a different side chain size or a different property (e.g., hydrophobic).

In the present application, the amino acid substitutions may also be conservative substitutions. The conservative substitutions may comprise changing amino acid residues in target proteins or polypeptides in a conservative form, for example, changing an amino acid residue with a certain side chain size or a certain property (e.g., hydrophilic) into another amino acid residue with the same or similar side chain size or the same or similar property (e.g., still hydrophilic). Such conservative substitutions generally do not greatly affect the structure or function of the resulting protein. In the present application, the amino acid sequence variant of the fusion protein or a fragment thereof may comprise conservative amino acid substitutions which do not significantly change the structure or function of the protein (e.g., a mutant of a human SIRPα variant 1 that blocks CD47 and specifically binds a CD47 protein).

As an example, the mutual substitutions of various amino acids in each group of the following groups can be considered as conservative substitutions in the present application: a group of amino acids with nonpolar side chains: alanine, valine, leucine, isoleucine, proline, phenylalanine, tryptophan and methionine; a group of uncharged amino acids with polar side chains: glycine, serine, threonine, cysteine, tyrosine, asparagine and glutamine; a group of negatively charged amino acids with polar side chains: aspartic acid and glutamic acid; positively charged basic amino acids: lysine, arginine and histidine; and amino acids carrying phenyl groups: phenylalanine, tryptophan and tyrosine.

In the present application, the mutant may comprise amino acid substitutions at amino acid residues selected from the group consisting of: (1) I61, V63, E77, E84, V93, L96, K98, N100 and V132; (2) I61, E77, Q82, K83 and E84; (3) I61, V63, K83, E84 and V132; (4) I61, E77, E84, R107 and V132; (5) I61, V63, E77, K83, E84 and N100; (6) I61, E77, Q82, K83, E84 and R107; (7) I61, E77, Q82, E84, V93, L96, N100, R107, G109 and V132; (8) I61, E77, Q82, K83, E84 and V132; (9) 161; (10) I61, D95, L96, G109 and V132; (11) I61, D95, L96, K98, G109 and V132; (12) I61, E77, E84, V93, R107 and V132; (13) E77, L96, N100, G109 and V132; (14) I61, V63, Q82, E84, D95, L96, N100 and V132; (15) I61, E77, Q82, K83, E84, V93, D95, L96, K98, N100 and V132; (16) I61, E77, Q82, K83, E84 and V93; (17) I61, V63, E77, K83, E84, D95, L96, K98 and N100; (18) I61, V63, E77, K83, D95, L96, K98, N100 and G109; (19) I61, E77, Q82, E84, V93, D95, L96, K98 and N100; and (20) I61, V63, E77, Q82 and E84.

In the present application, the mutant may comprise one or more (e.g., 1-2, 1-3, 1-4, 1-5, 1-6, 1-7, 1-8, 1-9, 1-10 or more) amino acid substitutions selected from the group consisting of: I61L/V/F, V63I, E77I/N/Q/K/H/M/R/N/V/L, Q82S/R/G/N, K83R, E84K/H/D/R/G, V93L/A, D95H/R/E, L96S/T, K98R, N100G/K/D/E, R107N/S, G109R/H and V132L/R/I/S.

In the present application, the amino acid substitution "XnY/Z" means that the residue X of site n in the corresponding amino acid sequence as shown in SEQ ID NO: 29 is substituted by an amino acid residue Y or an amino acid residue Z, in which n is a positive integer, X, Y and Z are the abbreviations of any amino acid residues independently, and X is different from Y or Z. For example, the amino acid substitution "I61L/V/F" means that the residue I of site 61 in the corresponding amino acid sequence as shown in SEQ ID NO: 29 is substituted by an amino acid residue L, V or F.

In the present application, the mutant may comprise amino acid substitutions selected from the group consisting of: (1) I61L, V63I, E77I, E84K, V93L, L96S, K98R, N100G and V132L; (2) I61V, E77N, Q82S, K83R and E84H; (3) I61F, V63I, K83R, E84K and V132I; (4) I61L, E77Q, E84D, R107N and V132I; (5) I61L, V63I, E77K, K83R, E84D and N100G; (6) I61V, E77H, Q82R, K83R, E84H and R107S; (7) I61L, E77I, Q82G, E84R, V93L, L96T, N100G, R107S, G109R and V132R; (8) I61L, E77M, Q82G, K83R, E84D and V132L; (9) I61L; (10) I61F, D95H, L96S, G109H and V132S; (11) I61F, D95H, L96S, K98R, G109H and V132S; (12) I61L, E77Q, E84D, V93A, R107N and V132I; (13) E77K, L96S, N100K, G109H and V132L; (14) I61L, V63I, Q82G, E84G, D95R, L96S, N100D and V132I; (15) I61L, E77R, Q82N, K83R, E84G, V93L, D95E, L96T, K98R, N100D and V132L; (16) I61V, E77N, Q82S, K83R, E84H and V93A; (17) I61V, V63I, E77V, K83R, E84D, D95E, L96T, K98R and N100E; (18) I61L, V63I, E77V, K83R, D95E, L96S, K98R, N100D and G109R; (19) I61V, E77L, Q82G, E84G, V93L, D95E, L96T, K98R and N100G; and (20) I61L, V63I, E77N, Q82G and E84G.

In the present application, based on the human SIRPα variant 1 (the amino acid sequence as shown in SEQ ID NO: 29, i.e., residues at site 33 to site 149 in the amino acid sequence of a human SIRPα), the mutants of the SIRPα variant 1 which comprise the amino acid substitutions of the above groups (1)-(20) respectively are named as Ml, M5, M12, M35, M37, M41, M57, M67, M81, M82, M84, M91, M99, M102, M111, M122, M126, M130, M135 and M145 successively. The mutants of the SIRPα variant 1 can successively comprise the amino acid sequences as shown in any one of SEQ ID NOs: 30-49.

In some embodiments, the mutant of the SIRPα variant 1 is M91, and the mutant of the SIRPα variant 1 comprises the amino acid sequence as shown in SEQ ID NO: 41.

The First Binding Domain that Specifically Binds PD-L1

In the present application, the first binding domain may comprise an antibody or an antigen-binding fragment or a variant thereof. For example, the antibody may be selected from the group consisting of: a monoclonal antibody, a single-chain antibody, a chimeric antibody, a humanized antibody and a fully human antibody. For example, the antigen-binding fragment is selected from the group consisting of: Fab, Fab', (Fab')2, F(ab)2, dAb, an isolated complementary determining region CDR, Fv and scFv.

The antibody or the antigen-binding fragment thereof of the present application may kill tumor cells and/or inhibit the tumor growth by specifically binding the PD-L1 protein. For example, the tumor may comprise a PD-L1 positive tumor. For example, the PD-L1 positive tumor may be selected from the group consisting of: gastric cancer, breast cancer, cervical cancer, lung cancer, head and neck tumor, melanoma, glioma, lymphoepithelioma, esophagus cancer or colorectal cancer. In the present application, the antibody and the antigen-binding fragment thereof can kill gastric cancer, breast cancer, cervical cancer, lung cancer, head and neck tumor, melanoma, glioma, lymphoepithelioma, esophagus cancer or colorectal cancer cells or inhibit the growth of gastric cancer, breast cancer, cervical cancer, lung cancer, head and neck tumor, melanoma, glioma, lymphoepithelioma, esophagus cancer or colorectal cancer cells.

The PD-L1 protein of the present application may be a human PD-L1 protein or a functional fragment thereof. For example, the PD-L1 protein may not be a mouse PD-L1 protein, or may not be a rat PD-L1 protein. In some embodiments, the antibody or the antigen-binding fragment thereof in the present application substantially does not bind the mouse PD-L1 protein or the rat PD-L1 protein.

The antibody or the antigen-binding fragment thereof in the present application can compete with the reference antibody to bind the PD-L1 protein. The reference antibody may comprise a light chain variable region and a heavy chain variable region. For example, the light chain variable region of the reference antibody may comprise LCDR1-3, the LCDR1 may comprise an amino acid sequence as shown in any one of the group consisting of: SEQ ID NO: 1 and SEQ ID NO: 15; the LCDR2 may comprise an amino acid sequence as shown in any one of the group consisting of: SEQ ID NO: 2 and SEQ ID NO: 16; and the LCDR3 may comprise an amino acid sequence as shown in any one of the group consisting of: SEQ ID NO: 3 and SEQ ID NO: 17. The heavy chain variable region of the reference antibody may comprise HCDR1-3, the HCDR1 may comprise an amino acid sequence as shown in any one of the group consisting of: SEQ ID NO: 4 and SEQ ID NO: 18; the HCDR2 may comprise an amino acid sequence as shown in any one of the group consisting of: SEQ ID NO: 5 and SEQ ID NO: 19; and the HCDR3 may comprise an amino acid sequence as shown in any one of the group consisting of: SEQ ID NO: 6 and SEQ ID NO: 20.

For example, the amino acid sequence of the light chain variable region of the reference antibody may comprise an amino acid sequence as shown in any one of the group consisting of: SEQ ID NO: 7 and SEQ ID NO: 21, and the amino acid sequence of the heavy chain variable region of the reference antibody may comprise an amino acid sequence as shown in any one of the group consisting of: SEQ ID NO: 8 and SEQ ID NO: 22. Further for example, the light chain of the reference antibody may comprise an amino acid sequence as shown in any one of the group consisting of: SEQ ID NO: 11 and SEQ ID NO: 25; and the heavy chain of the reference antibody may comprise an amino acid sequence as shown in any one of the group consisting of: SEQ ID NO: 13 and SEQ ID NO: 27. For example, the light chain of the reference antibody may comprise an amino acid sequence as shown in SEQ ID NO: 11, and the heavy chain of the reference antibody may comprise an amino acid sequence as shown in SEQ ID NO: 13. For example, the light chain of the reference antibody may comprise an amino acid sequence as shown in SEQ ID NO: 25, and the heavy chain of the reference antibody may comprise an amino acid sequence as shown in SEQ ID NO: 27.

The antibody or the antigen-binding fragment thereof in the present application may comprise a light chain of the antibody or a fragment thereof. For example, the light chain of the antibody or the fragment thereof may comprise a Igκ constant region, e.g., it may comprise a human Igκ constant region.

For example, the light chain of the antibody or the fragment thereof may comprise LCDR1, and the LCDR1 may comprise an amino acid sequence as below: SEQ ID NO: 1. The light chain of the antibody or the fragment thereof may comprise LCDR2, and the LCDR2 may comprise an amino acid sequence as below: SEQ ID NO: 2. The light chain of the antibody or the fragment thereof may comprise LCDR3, and the LCDR3 may comprise an amino acid sequence as below: SEQ ID NO: 3. Further for example, the light chain of the antibody or the fragment thereof may comprise LCDR1, and the LCDR1 may comprise an amino acid sequence as below: SEQ ID NO: 15. The light chain of the antibody or the fragment thereof may comprise LCDR2, and the LCDR2 may comprise an amino acid sequence as below: SEQ ID NO: 16. The light chain of the antibody or the fragment thereof may comprise LCDR3, and the LCDR3 may comprise an amino acid sequence as below: SEQ ID NO: 17.

The light chain of the antibody or the fragment thereof in the present application may comprise a light chain variable region VL, and the amino acid sequence of the light chain variable region VL may be: SEQ ID NO: 7. In some embodiments, the amino acid sequence of the light chain of the antibody or the fragment thereof may be: SEQ ID NO: 11. Further for example, the amino acid sequence of the light chain variable region VL may be: SEQ ID NO: 21. In some embodiments, the amino acid sequence of the light chain of the antibody or the fragment thereof may be: SEQ ID NO: 25.

The antibody or the antigen-binding fragment thereof in the present application may comprise a heavy chain of the antibody or a fragment thereof. For example, the heavy chain of the antibody or the fragment thereof further comprises a human constant region. Wherein, the human constant region may comprise a human IgG constant region. Wherein, the IgG constant region may comprise a human IgG1 constant region or IgG4.

For example, the heavy chain of the antibody or the fragment thereof may comprise HCDR1, and the HCDR1 may comprise an amino acid sequence as below: SEQ ID NO: 4. The heavy chain of the antibody or the fragment thereof may comprise HCDR2, and the HCDR2 may comprise an amino acid sequence as below: SEQ ID NO 5. The heavy chain of the antibody or the fragment thereof may comprise HCDR3, and the HCDR3 may comprise an amino acid sequence as below: SEQ ID NO: 6. Further for example, the heavy chain of the antibody or the fragment thereof may comprise HCDR1, and the HCDR1 may comprise an amino acid sequence as below: SEQ ID NO: 18. The heavy chain of the antibody or the fragment thereof may comprise HCDR2, and the HCDR2 may comprise an amino acid sequence as below: SEQ ID NO 19. The heavy chain of the antibody or the fragment thereof may comprise HCDR3, and the HCDR3 may comprise an amino acid sequence as below: SEQ ID NO: 20.

The heavy chain of the antibody or the fragment thereof may comprise a heavy chain variable region VH, and the heavy chain variable region VH may comprise an amino acid sequence as below: SEQ ID NO: 8. In some embodiments, the heavy chain of the antibody may comprise an amino acid sequence as below: SEQ ID NO: 13. Further for example, the heavy chain variable region VH may comprise an amino acid sequence as below: SEQ ID NO: 22. In some embodiments, the heavy chain of the antibody may comprise an amino acid sequence as below: SEQ ID NO: 27.

In some embodiments, the amino acid sequence of the light chain of the antibody or the antigen-binding fragment thereof in the present application comprises SEQ ID NO: 11; and the amino acid sequence of its heavy chain comprises SEQ ID NO: 13; or the amino acid sequence of the light chain of the antibody or the antigen-binding fragment thereof in the present application comprises SEQ ID NO: 25; and the amino acid sequence of its heavy chain comprises SEQ ID NO: 27.

In some embodiments, the amino acid sequence of LCDR1 in the antibody or the antigen-binding fragment thereof of the present application may comprise SEQ ID NO: 1; the amino acid sequence of LCDR2 may comprise SEQ ID NO: 2; the amino acid sequence of LCDR3 may comprise SEQ ID NO: 3; and the amino acid sequence of HCDR1 may comprise SEQ ID NO: 4; or the amino acid sequence of HCDR2 may comprise SEQ ID NO: 5; the amino acid sequence of HCDR3 may comprise SEQ ID NO: 6. For example, the antibody or the antigen-binding fragment thereof may comprise an antibody SG1201 or an antibody having the same LCDR1-3 and HCDR1-3 as those in the antibody SG1201. In some embodiments, the light chain of the antibody or the antigen-binding fragment thereof in the present application may comprise a light chain variable region, and the amino acid sequence of the light chain variable region may comprise SEQ ID NO: 7; and its heavy chain may comprise a heavy chain variable region, and the amino acid sequence of the heavy chain variable region may comprise SEQ ID NO: 8. For example, the antibody or the antigen-binding fragment thereof may comprise an antibody SG1201 or an antibody having the same light chain variable region and heavy chain variable region as those in the antibody SG1201. In some embodiments, the antibody or the antigen-binding fragment thereof of the present application may comprise a light chain and a heavy chain, the amino acid sequence of the light chain is shown in SEQ ID NO: 11 and the amino acid sequence of the heavy chain is shown in SEQ ID NO: 13. For example, the antibody or the antigen-binding fragment thereof may comprise an antibody SG1201 or have the same light chain and heavy chain amino acid sequences as those in the antibody SG1201.

In some embodiments, the antibody of the present application may be SG1201. The amino acid sequences of LCDR1-3 in the antibody SG1201 are shown in SEQ ID NO: 1, SEQ ID NO: 2 and SEQ ID NO: 3 respectively; the amino acid sequence of VL is shown in SEQ ID NO: 7; the amino acid sequence of the light chain is shown in SEQ ID NO: 11; the amino acid sequences of HCDR1-3 are shown in SEQ ID NO: 4, SEQ ID NO: 5 and SEQ ID NO: 6 respectively; the amino acid sequence of VH is shown in SEQ ID NO: 8; and the amino acid sequence of the heavy chain is shown in SEQ ID NO: 13.

In some embodiments, the amino acid sequence of LCDR1 in the antibody or the antigen-binding fragment thereof of the present application may comprise SEQ ID NO: 15; the amino acid sequence of LCDR2 may comprise SEQ ID NO: 16; the amino acid sequence of LCDR3 may comprise SEQ ID NO: 17; and the amino acid sequence of HCDR1 may comprise SEQ ID NO: 18; the amino acid sequence of HCDR2 may comprise SEQ ID NO: 19; the amino acid sequence of HCDR3 may comprise SEQ ID NO: 20. For example, the antibody or the antigen-binding fragment thereof may comprise an antibody SG1202 or an antibody having the same LCDR1-3 and HCDR1-3 as those in the antibody SG1202. In some embodiments, the light chain of the antibody or the antigen-binding fragment thereof in the present application may comprise a light chain variable region, and the amino acid sequence of the light chain variable region may comprise SEQ ID NO: 21; and its heavy chain may comprise a heavy chain variable region, the amino acid sequence of the heavy chain variable region may comprise SEQ ID NO: 22. For example, the antibody or the antigen-binding fragment thereof may comprise an antibody SG1202 or an antibody having the same light chain variable region and heavy chain variable region as those in the antibody SG1202. In some embodiments, the antibody or the antigen-binding fragment thereof in the present application may comprise a light chain and a heavy chain, the amino acid sequence of the light chain is shown in SEQ ID NO: 25 and the amino acid sequence of the heavy chain is shown in SEQ ID NO: 27. For example, the antibody or the antigen-binding fragment thereof may comprise an antibody SG1202 or have the same light chain and heavy chain amino acid sequences as those in the antibody SG1202.

In some embodiments, the antibody of the present application may be SG1202. The amino acid sequences of LCDR1-3 of the antibody SG1202 are shown in SEQ ID NO: 15, SEQ ID NO: 16 and SEQ ID NO: 17, respectively; the amino acid sequence of VL is shown in SEQ ID NO: 21; the amino acid sequences of HCDR1-3 are shown in SEQ ID NO: 18, SEQ ID NO: 19 and SEQ ID NO: 20, respectively; the amino acid sequence of VH is shown in SEQ ID NO: 22; the amino acid sequence of the light chain is shown in SEQ ID NO: 25; and the amino acid sequence of the heavy chain is shown in SEQ ID NO: 27.

The antibody or the antigen-binding fragment thereof in the present application may also comprise one or more random mutations (e.g., one or more, e.g. one or several amino acid substitutions) in the amino acid sequence of the light chain and/or the heavy chain of SG1201 and/or SG1202. For example, the antibody or the antigen-binding fragment thereof may comprise one or more random mutations (e.g., one or more, e.g. one or several amino acid substitutions) at one or more sites of framework regions L-FR1-4 in the light chain variable region of SG1201 and/or SG1202, and/or comprise one or more random mutations (e.g., one or more, e.g. one or several amino acid substitutions) at one or more sites of framework regions H-FR1-4 in the heavy chain variable region of SG1201 and/or SG1202.

The Linkage Between the First Binding Domain and the Second Binding Domain

In the present application, the first binding domain may be located at the N-terminal of the second binding domain. For example, the C-terminal of the first binding domain may be linked to the N-terminal of the second binding domain indirectly through a linker. In some instances, the C-terminal of the first binding domain may also be linked to the N-terminal of the second binding domain directly (e.g., in-frame).

In the present application, the fusion protein may also comprise a linker, which may be located at the C-terminal of the first binding domain and located at the N-terminal of the second binding domain. For example, in the fusion protein, the C-terminal of the first binding domain may be linked to the N-terminal of the linker, and the C-terminal of the linker may be linked to the N-terminal of the second binding domain. For example, the first binding domain, the linker and the second binding domain can be comprised in the fusion protein successively from N-terminal to C-terminal.

In the present application, the linker may comprise an amino acid sequence as shown in SEQ ID NO:52.

In some instances, the fusion protein may comprise at least 2 (e.g., at least 2, at least 3, at least 4, at least 5, at least 6, at least 7, at least 8, at least 9, at least 10, or more) of the second binding domain. In the present application, each of the second binding domains can be located at the C-terminal of the first binding domain respectively. In the present application, the more than two second binding domains can be linked to the C-terminal of the first binding domain directly or indirectly.

In the present application, the fusion protein may comprise a first binding domain that specifically binds PD-L1, and a second binding domain that specifically binds a CD47 protein, in which the second binding domain may comprise a mutant of a human SIRPα variant 1, the C-terminal of the antibody that specifically binds PD-L1 or the antigen-binding fragment or the variant thereof can be directly or indirectly linked to the N-terminal of the mutant of the human SIRPα variant 1. For example, the second binding domain may comprise at least two mutants of the human SIRPα variant 1, and the N-terminals of the two mutants of the human SIRPα variant 1 are linked to the C-terminals of the antibody that specifically binds PD-L1 or the antigen-binding fragment or the variant thereof, respectively.

For example, as shown in FIG. 1, the first binding domain of the fusion protein (SG12473) may comprise SG1201, and the second binding domain thereof may comprise two mutants M91 of the SIRPα variant 1, the sequence of the used linker 1 is shown in SEQ ID NO: 52, the N-terminals of the two M91 are linked to the C-terminals of two heavy chains of SG1201 through the linker 1 respectively. In the fusion protein, M91 is linked to the C-terminal of the heavy chain of SG1201 to get the second polypeptide chain, and the light chain of SG1201 may be named as the first polypeptide chain. The amino acid sequences of the second polypeptide chain and the first polypeptide chain of SG12473 are shown in SEQ ID NO: 53 and SEQ ID NO: 11 respectively.

For example, as shown in FIG. 1, the first binding domain of the fusion protein (SG12474) may comprise SG1202, the second binding domain thereof may comprise two mutants M91 of the SIRPα variant 1, the sequence of the used linker 1 is shown in SEQ ID NO: 52, the N-terminals of the two M91 are linked to the C-terminals of two heavy chains of SG1202 through the linker 1 respectively. In the fusion protein, M91 is linked to the C-terminal of the heavy chain of SG1202 to get the second polypeptide chain, and the light chain of SG1202 may be named as the first polypeptide chain. The amino acid sequences of the second polypeptide chain and the first polypeptide chain of SG12474 are shown in SEQ ID NO: 54 and SEQ ID NO: 25 respectively.

Nucleic Acid Molecule, Vector and Cell as Well as Preparation Method

In another aspect, the present application provides one or more isolated nucleic acid molecules, which encode the fusion protein or the immunoconjugate. For example, each nucleic acid molecule of the one or more nucleic acid molecules may encode the whole antibody or the antigen-binding fragment thereof, and may also encode a part thereof (e.g., one or more of HCDR1-3, LCDR1-3, VL, VH, light chains or heavy chains).

The nucleic acid molecule of the present application may be isolated. For example, they can be produced or synthesized by the processes below: (i) amplification in vitro, for example being produced by amplification through polymerase chain reaction (PCR), (ii) being produced by cloning recombination, (iii) being purified, for example fractioned by enzymatic digestion and gel electrophoresis, or, (iv) being synthesized, for example through chemical synthesis. In some embodiments, the isolated nucleic acid is a nucleic acid molecule prepared by a recombinant DNA technology.

Recombinant DNA and molecular cloning techniques comprise those described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan and L. W. Enquist, Experiments with Gene Fusions, Cold Spring Harbor Laboratory, Cold Spring Harbor, N.Y. (1984) as well as by Ausubel, F. M. et al, Current Protocols in Molecular Biology, pub. by Greene Publishing Assoc. and Wiley-Interscience (1987). In brief, the nucleic acids can be prepared from genomic DNA fragments, cDNA and RNA, and all of these nucleic acids can be extracted from cells directly or produced by recombination through various amplification methods (including, but not limited to, PCR and RT-PCR).

The direct chemical synthesis of nucleic acids generally involves sequentially adding 3'-capped and 5'-capped nucleotide monomers into the terminal 5'-hydroxyl of the growing nucleotide polymer chain, in which each addition is realized by nucleophilic attacking the terminal 5'-hydroxyl of the growth chain at 3'-position of the added monomers, and the monomers are generally phosphorus derivatives, such as phosphotriester, phosphoramidite, etc. See, for example, Matteuci et al, Tet. Lett. 521:719 (1980); U.S. Pat. No. 4,500,707 to Caruthers et al; and U.S. Pat. Nos. 5,436,327 and 5,700,637 to Southern et al. In another aspect, the present application provides a vector comprising the isolated polynucleotide of the present application. The vector may be any linear nucleic acid, plasmid, phagemid, cosmid, RNA vector, viral vector, and the like. Non-limiting examples of the viral vector may comprise a retrovirus, an adenovirus and an adeno-associated virus. In some embodiments, the vector is an expression vector, for example, a phage display vector.

In another aspect, the present application provides one or more vectors including the nucleic acid molecules. For example, the vector may comprise the one or more nucleic acid molecules of the present application. Each vector may comprise one or more of the nucleic acid molecules. In addition, the vector may further comprise other genes, such as marker genes which allow to select the vector in appropriate host cells and under appropriate conditions. In addition, the vector may further comprise an expression control element allowing the correct expression of the coding regions in an appropriate host. Such a control element is well known to those of ordinary skills in the art. For example, it may comprise promoters, ribosome bind sites, enhancers and other control elements for regulating gene transcription or mRNA translation, and the like. In some embodiments, the expression control sequences are tunable elements. The specific structures of the expression control sequences may change depending on the species or the functions of cell types, but generally comprise 5'-non-transcribed sequences and 5' and 3'-non-translated sequences which participate in the initiation of transcription and translation respectively, e.g., TATA cassettes, capped sequences, CAAT sequences, etc. For example, 5'-non-transcribed expression control sequence may comprise a promoter region, which may comprise a promoter sequence for transcribing and controlling the functionally linked nucleic acids. The expression control sequence may further include an enhancer sequence or an upstream activator sequence. In the present application, suitable promoters may comprise, for example, promoters for SP6, T3 and T7 polymerases, a human U6RNA promoter, a CMV promoter and an artificial hybrid promoter (e.g., CMV), in which a certain part of the promoter may be fused with a certain part of the gene promoter of other cell proteins (e.g., human GAPDH, glyceraldehyde-3-phosphate dehydrogenase), and it may comprise or not comprise additional introns. The one or more nucleic acid molecules of the present application can be linked with the expression control elements operably.

The vector may comprise, for example, a plasmid, a cosmid, a virus, a phage or other vectors commonly used in genetic engineering for example. In some embodiments, the vector may be an expression vector.

The vector can also contain one or more selective marker genes, which, after the expression, can confer one or more phenotypic traits that can be used to select or identify host cells carrying the vector in other ways. Non-limiting examples of suitable selective markers for eukaryocytes comprise dihydrofolate reductase and neomycin resistance.

In another aspect, the present application provides a cell, which comprises the fusion protein, the immunoconjugate, the nucleic acid molecule, or the vector. The cell may be a host cell. For example, the cell may comprise various cell types as below: prokaryotic cells such as *Escherichia coli* or *Bacillus subtilis*, fungal cells such as yeast cells or *Aspergillus*, insect cells such as S2 Drosophila cells or Sf9, or animal cells such as fibroblasts, CHO cells, COS cells, NSO cells, HeLa cells, BHK cells, HEK 293 cells or human cells.

For example, the vector can be introduced into the host cell stably or transiently through a variety of established technologies. For example, one method involves calcium chloride treatment, in which the vector is introduced through calcium precipitation. Other salts can also be used following similar methods, for example calcium phosphate. In addition, electroporation (i. e., applying electric current to increase the permeability of cells to nucleic acids) can be used. Other examples of transformation methods comprise microinjection, DEAE dextran-mediated transformation and heat shock in the presence of lithium acetate. Lipid complexes, liposomes and dendrimers can also be used to transfect host cells.

When heterogenous sequences are introduced into a host cell, a variety of methods can be applied to identify host cells into which the vector has been introduced. One exemplary selection method comprises subculturing a single cell to form a single colony, then testing the expression of the desired protein product. Another method requires the selection of the host cell containing a heterogenous sequence based on the phenotypic traits conferred by the expression of selective marker genes included within the vector.

For example, the introduction of various heterogenous sequences of the present application into the host cell can be confirmed by the following methods such as PCR, Southern blotting or Northern blotting hybridization. For example, nucleic acids can be prepared from the obtained host cell, and specific target sequences can be amplified by PCR using primers that are specific to the target sequences. The amplified products are subjected to agarose gel electrophoresis, polyacrylamide gel electrophoresis or capillary electrophoresis, then stained with ethidium bromide, SYBR Green solution or the like, or detected for DNA by means of UV detection. Alternatively, nucleic acid probes that are specific to the target sequences can be used in hybridization reactions. The expression of specific gene sequences can be determined by hybridization with PCR or Northern blotting or by the reverse transcription detection of corresponding mRNA using immunoassays of antibodies that react with the encoded gene products. Exemplary immunoassays comprise, but not limited to, ELISA, radioimmunoassay and sandwich immunoassay.

In addition, the introduction of various heterogenous sequences of the present application into the host cell can be confirmed by the enzymatic activity of enzymes (e.g., enzymatic markers) that are encoded with heterogenous sequences. Enzymes can be determined by various methods known in the art. Generally, enzymatic activity can be determined by the formation of the products or by the transformation of the substrate of the enzymatic reaction under investigation. The reaction can be performed in vitro or in vivo.

In another aspect, the present application provides a method of preparing the fusion protein, which may comprise culturing the cell under a condition enabling the expression of the fusion protein. For example, suitable culture media, suitable temperature and culture time could be used, and all these methods are known to those of ordinary skills in the art.

In some instances, the method may further comprise steps of separating and/or purifying the fusion protein. For example, the fusion protein of the present application can be purified and isolated by affinity chromatography using protein G-agarose or protein A-agarose, or by gel electrophoresis and/or high performance liquid chromatography.

Immunoconjugate, Composition and Application

In another aspect, the present application provides an immunoconjugate comprising the fusion protein. For example, the immunoconjugate may be fusion protein-drug conjugate (ADC), in which the fusion protein of the present application is conjugated with one or more therapeutic agents, and the therapeutic agents comprise, but not limited to, cytotoxic agents, radiotoxic agents (e.g., radioisotopes) and/or immune inhibitors (e.g., any agents that kill cells by means of inhibiting immune responses) and the like. In some embodiments, the therapeutic agents may be those capable of treating tumor-associated diseases or disorders.

The conjugation can be performed by a peptide linker (e.g., a cleavable linker) or through other ways. For example, the linker may be an acid labile linker, a peptidase sensitive linker, a photolabile linker, and the like.

In another aspect, the present application provides a composition comprising the fusion protein, the immunoconjugate, or the nucleic acid molecule, and optionally, pharmaceutically acceptable excipients.

For example, the pharmaceutically acceptable excipients may comprise buffering agents, antioxidants, preservatives, low molecular weight polypeptides, proteins, hydrophilic polymers, amino acids, sugar, chelating agents, counter ions, metal complexes and/or nonionic surfactants and the like.

In the present application, the composition can be formulated with pharmaceutically acceptable carriers or diluents and any other known auxiliary agents and excipients by conventional technical means in this field, for example following the technology disclosed in Remington: The Science and Practice of Pharmacy, Edition 19, Gennaro ed., Mack Publishing Co., Easton, Pa., 1995.

In the present application, the composition can be formulated for oral administration, intravenous administration, intramuscular administration, in situ administration at tumor sites, inhalation, rectal administration, vaginal administration, transdermal administration or administration by subcutaneous reservoir.

For example, the composition can be used to inhibit the tumor growth. For example, the composition of the present application can inhibit or delay the development or progress of diseases, reduce the size of tumors (even essentially eliminating tumors), and/or relieve and/or stabilize the status of diseases.

For example, the composition of the present application may be suitable forms for oral administration, such as tablets, capsules, pills, powders, sustained release preparations, solutions, suspensions; or for parenteral injection, such as sterile solutions, suspensions or emulsions; or for local administration as ointment or cream; or for rectal administration as suppositories. The composition may be unit dose forms suitable for single dose at precise dosages. The composition may further comprise conventional drug carriers or excipients. In addition, the composition may comprise other drugs or agents, carriers, adjuvants, etc.

The composition of the present application may comprise a therapeutically effective amount of the fusion protein. The therapeutically effective amount is a dosage required for preventing and/or treating (at least partially treating) diseases or disorders (e.g., tumors) and/or any complications thereof in a subject suffering from or being at risk of these diseases or disorders. The specific amount/concentration of the dosage may change depending on the administration method and the demand of the patient, and can be determined, for example, based on the size of the patient, the viscosity and/or the body weight. For example, a suitable dosage may be about 0.1 mg or 1 mg/kg/day to about 50 mg/kg/day; sometimes, the dosage may be higher. It should be understood that these specific dosages can be adjusted conveniently by persons skilled in the art (e.g., doctors or pharmacists) based on the specific patient, preparations and/or the status of disease.

In the present application, the terms "treating" or "curing" or "relieving" or "improving" can be used interchangeably in the present application, and refer to those methods capable of obtaining beneficial or desired results (including, but not limited to, therapeutic benefits and/or preventive benefits). In the present application, the therapeutic benefits generally refer to eradicating or reducing the severity of the underlying conditions being treated. In addition, therapeutic benefits are realized by eradicating or reducing the severity of the underlying conditions or reducing the incidence of one or more physical symptoms associated with the underlying conditions so as to observe improvements in the subject (although the subject may still suffer from the underlying conditions). With regard to the preventive benefits, the composition can be administered to the subject at risk of developing a specific disease or the subject with one or more physical symptoms of the reported disease, even if the disease may not have been diagnosed.

In another aspect, the present application provides a use of the fusion protein, the immunoconjugate, the nucleic acid molecule, the vector, the composition, or the cell in the preparation of a medicament, in which the medicament may be used for treating a tumor.

In another aspect, the fusion protein, the immunoconjugate, the nucleic acid molecule, the vector, the composition or the cell of the present application may be used for treating the tumor.

In another aspect, the present application provides a method of treating a tumor, including administering to the subject the fusion protein, the immunoconjugate, the nucleic acid molecule, the vector, the composition or the cell of the present application.

In another aspect, the present application provides a method of blocking the interaction between CD47 protein and SIRPα, including administering (for example, administering to a subject in need thereof or cells or biological samples) the fusion protein or the composition of the present application.

In another aspect, the present application provides a method of blocking the interaction between PD-L1 and PD1, including administering (for example, administering to a subject in need thereof or cells or biological samples) the fusion protein or the composition of the present application.

In another aspect, the present application provides a method of inhibiting a tumor or the growth and/or proliferation of tumor cells, including contacting the fusion protein or the composition of the present application with the tumor or the tumor cells. For example, the contact may be in vitro.

In another aspect, the present application provides a method capable of inhibiting a tumor or the growth and/or proliferation of tumor cells, including administering to a subject in need thereof an effective amount of the fusion protein, the immunoconjugate, the nucleic acid molecule, the vector, the composition, or the cell.

In some embodiments, the tumor may comprise a solid tumor and a non-solid tumor.

In some embodiments, the solid tumor and the non-solid tumor may comprise multiple myeloma, leukemia, Non-Hodgkin's lymphoma, Hodgkin's lymphoma, neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer, frontal sinus tumor, hypopharyngeal cancer, olfactory neuroblastoma, tongue cancer, gingival carcinoma, ampulla carcinoma, colon cancer, rectal cancer, kidney cancer, ureteral carcinoma, bladder cancer, penile cancer, fallopian tube carcinoma, eyelid cancer, retinoblastoma.

In another aspect, the present application provides the fusion protein, the immunoconjugate, the nucleic acid molecule, the vector, the composition, or the cell, which can be used for treating a tumor or an autoimmune disease In the present application, the term "subject" generally refers to human or non-human animals, including, but not limited to, cat, dog, horse, pig, cow, sheep, goat, rabbit, mouse, rat or monkey.

Without intending to be bound by any theory, the embodiments below are only for interpreting the fusion protein, the preparation method and the use of the present application, rather than limiting the inventive scope of the present application.

EXAMPLES

Example 1 Construction of the Fusion Protein

Referring to the fusion protein structure as shown in FIG. 1, taking Roche's PD-L1 antibody Atezolizumab (SG1201) and the mutant M91 (SEQ ID: NO 41) of the SIRPα variant 1 for example, the selected linker 1 (SEQ ID: NO 52) is used from N terminal to C terminal to successively link SG1201, the linker and two M91, in which the N-terminals of the two M91 are linked to the C-terminal of the heavy chain of SG1201 respectively, so as to get the fusion protein SG12473.

The amino acid sequences of LCDR1-3 of the antibody SG1201 are shown in SEQ ID NO: 1, SEQ ID NO: 2 and SEQ ID NO: 3, respectively; the amino acid sequence of VL is shown in SEQ ID NO: 7; the nucleotide sequence encoding VL is shown in SEQ ID NO: 9; the amino acid sequences of HCDR1-3 of the antibody SG1201 are shown in SEQ ID NO: 4, SEQ ID NO: 5 and SEQ ID NO: 6, respectively; the amino acid sequence of VH is shown in SEQ ID NO: 8; the nucleotide sequence encoding VH is shown in SEQ ID NO: 10. The amino acid sequence of the light chain of the antibody SG1201 is shown in SEQ ID NO: 11; and the nucleotide sequence encoding its light chain is shown in SEQ ID NO: 12. The amino acid sequence of the heavy chain of the antibody SG1201 is shown in SEQ ID NO: 13; and the nucleotide sequence encoding its heavy chain is shown in SEQ ID NO: 14.

The fusion protein SG12473 is composed of a first polypeptide chain and a second polypeptide chain, in which the first polypeptide chain is the light chain of SG1201, the amino acid sequence of which is shown in SEQ ID NO: 11; the second polypeptide chain is the polypeptide chain obtained from the linkage between the heavy chain of SG1201 with a mutation in Fc region and M91 through the linker 1, the amino acid sequence of which is shown in SEQ ID NO: 53.

Referring to the fusion protein structure as shown in FIG. 1, taking AstraZeneca PD-L1 antibody Durvalumab (SG1202) and the mutant M91 (SEQ ID: NO 41) of the SIRPα variant 1 for example, the selected linker 1 (SEQ ID: NO 52) is used from N terminal to C terminal to successively link SG1202, the linker and two M91, in which the N-terminals of the two M91 are linked to the C-terminal of the heavy chain of SG1202 respectively, so as to get the fusion protein SG12474.

The amino acid sequences of LCDR1-3 of the antibody SG1202 are shown in SEQ ID NO: 15, SEQ ID NO: 16 and SEQ ID NO: 17, respectively; the amino acid sequence of VL is shown in SEQ ID NO: 21; the nucleotide sequence encoding VL is shown in SEQ ID NO: 23; the amino acid sequences of HCDR1-3 of the antibody SG1202 are shown in SEQ ID NO: 18, SEQ ID NO: 19 and SEQ ID NO: 20, respectively; the amino acid sequence of VH is shown in SEQ ID NO: 22; the nucleotide sequence encoding VH is shown in SEQ ID NO: 24. The amino acid sequence of the light chain of the antibody SG1202 is shown in SEQ ID NO: 25; the nucleotide sequence encoding its light chain is shown in SEQ ID NO: 26. The amino acid sequence of the heavy chain of the antibody SG1202 is shown in SEQ ID NO: 27; and the nucleotide sequence encoding its heavy chain is shown in SEQ ID NO: 28.

The fusion protein SG12474 is composed of a first polypeptide chain and a second polypeptide chain, in which the first polypeptide chain is the light chain of SG1202, the amino acid sequence of which is shown in SEQ ID NO: 25; the second polypeptide chain is the polypeptide chain obtained from the linkage between the heavy chain of SG1202 with a mutation in Fc region and M91 through the linker 1, the amino acid sequence of which is shown in SEQ ID NO: 54.

Wherein, the amino acid sequence of IgG1-Fc is shown in SEQ ID NO: 50; and the amino acid sequence of Fc with a mutation is shown in SEQ ID NO: 51.

The fusion protein SS002M91 between the mutant M91 (SEQ ID: NO 41) of the SIRPα variant 1 and IgG1-Fc is a homodimer, and the amino acid sequence of its monomer is shown in SEQ ID NO: 55.

Example 2 Detection on the Activity of Binding Two Antigens (1) With a humanized antibody against different antigens as the control, the binding activity between a corresponding bifunctional protein and a related antigen was evaluated by ELISA.

PD-L1 (human-derived, PD-L1/B7-H1/CD274 Protein (His Tag) purchased from Sino Biological Co.) was coated with ELISA strips at 4° C. overnight; after washing with PBST, 10% of fetal calf serum was added and blocked at 37° C. for 1 hour; different concentrations of the antibody SG1201 and the fusion protein SG12473, or different concentrations of the antibody SG1202 and the fusion protein SG12474 were added and reacted at 37° C. for 1 hour; after washing with PBST, a horseradish peroxidase-labeled goat anti-human IgG secondary antibody (Goat Anti human IgG HRP, Thermo Fisher Scientific) was added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N H2504 stop solution to terminate the reaction of the substrate, OD values were read at 450 nm on the microplate reader, and the capacity of the bifunctional protein to bind the related target antigen was analyzed.

Figure 2:
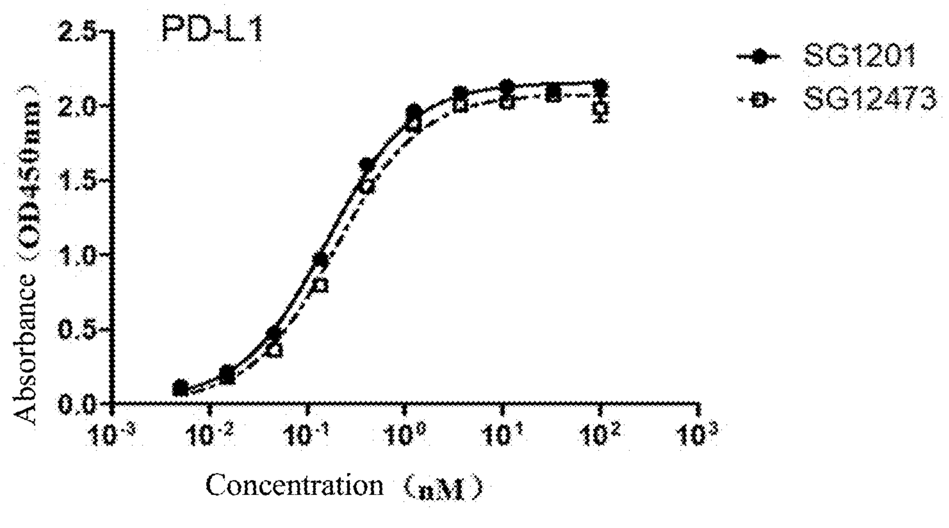
FIGS. 2-3 show the binding ability of the fusion protein to PD-L1 according to the present application.
Figure 3:
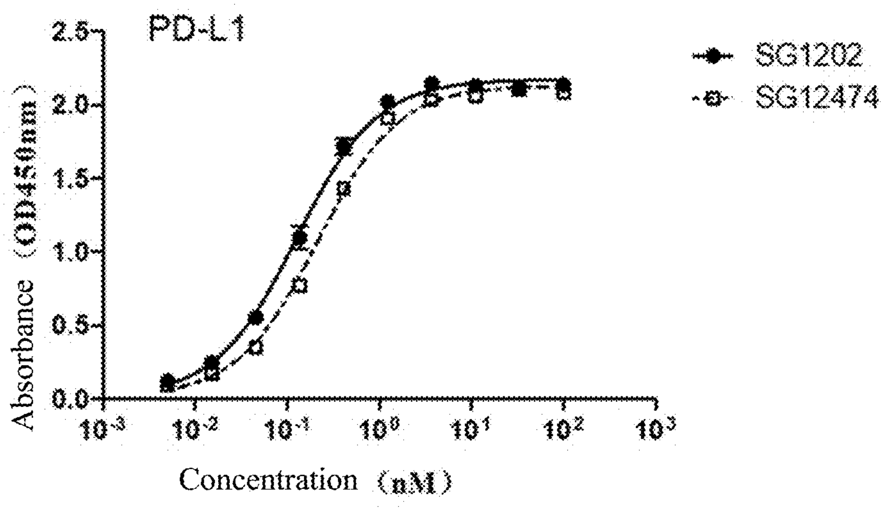

The results were shown in FIGS. 2-3. FIGS. 2-3 showed that although the antibody types of PD-L1 in the fusion protein SG12473 and the fusion protein SG12474 were different, the capacities of the fusion protein SG12473 and the fusion protein SG12474 to bind PD-L1 were not affected.

(2) With the mutant M91 of the CD47 receptor as the control, the binding activity between a corresponding bifunctional protein and CD47 was evaluated by ELISA.

CD47 (human-derived, CD47 Protein (His Tag) purchased from Sino Biological Co.) was coated with ELISA strips at 4° C. overnight; after washing with PBST, 10% of fetal calf serum was added and blocked at 37° C. for 1 hour; different concentrations of the fusion protein SS002M91, the fusion protein SG12473 and the fusion protein SG12474 were added and reacted at 37° C. for 1 hour; after washing with PBST, a horseradish peroxidase-labeled goat anti-human IgG secondary antibody (Goat Anti human IgG HRP, Thermo Fisher Scientific) was added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N H2504 stop solution to terminate the reaction of the substrate, OD values were read at 450 nm on the microplate reader, and the capacity of the fusion protein SG12473 and the fusion protein SG12474 to bind CD47 was analyzed.

Figure 4:
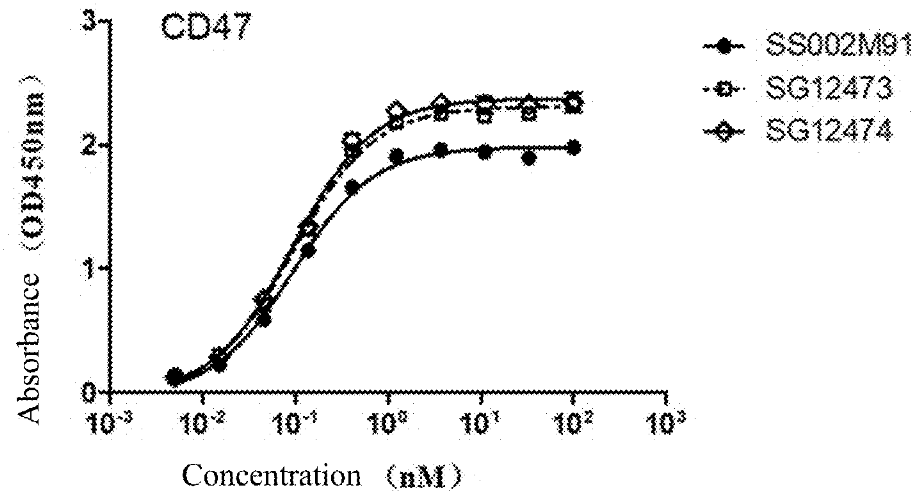
FIG. 4 shows the binding ability of the fusion protein to CD47 according to the present application.

The results were shown in FIG. 4. FIG. 4 showed that although the antibody types of PD-L1 in the fusion protein SG12473 and the fusion protein SG12474 were different, the capacities of the fusion protein SG12473 and the fusion protein SG12474 to bind CD47 were not affected.

Example 3 Detection on the Activity of Simultaneously Binding Two Antigens

With a humanized antibody against different antigens as the control, the biological activity of the fusion protein SG12473 and the fusion protein SG12474 to simultaneously bind two antigens was evaluated by ELISA.

PD-L1 was coated with ELISA strips at 4° C. overnight; after washing with PBST, 10% of fetal calf serum was added and blocked at 37° C. for 1 hour; different concentrations of the antibody SG1201, the fusion protein SG12473, the antibody SG1202 and the fusion protein SG12474 were added and reacted at 37° C. for 1 hour; after washing with PBST, biotin-labeled CD47 (Biotin-Fc-CD47) was added and reacted at 37° C. for 30 minutes, and washed with PBST for 5 times; horseradish peroxidase-labeled avidin (Streptavidin-HRP, Jiaxuan Bio.) was added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N $H_2SO_4$ stop solution to terminate the reaction of the substrate, OD values were read at 450 nm on the microplate reader, and the capacities of the fusion protein SG12473 and the fusion protein SG12474 to simultaneously bind PD-L1 and CD47 were analyzed.

Figure 5:
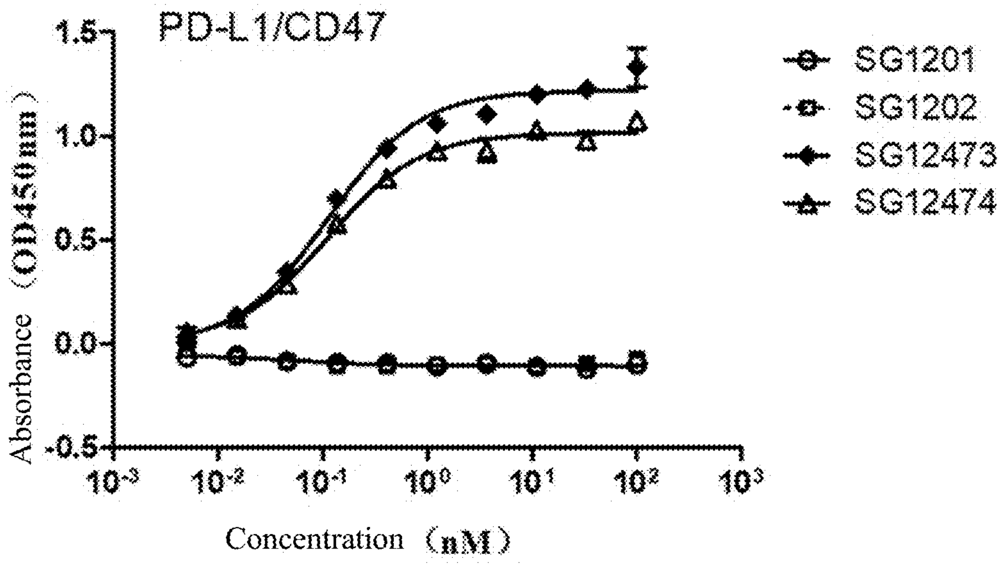
FIG. 5 shows the binding ability of the fusion protein to PD-L1 and CD47 simultaneously according to the present application.

The results were shown in FIG. 5. FIG. 5 showed that although the antibody types of PD-L1 in the fusion protein SG12473 and the fusion protein SG12474 were different, the capacities of the fusion protein SG12473 and the fusion protein SG12474 to simultaneously bind PD-L1 and CD47 were not affected.

Example 4 Analysis on the Activity of Blocking the CD47/SIRPα Interaction

With the fusion protein SS002M91 as the control, the biological activities of the fusion proteins SG12473 and SG12474 to block the CD47/SIRPα interaction were evaluated.

SIRPα-His was coated on the assay plate at 1 ug/ml overnight at 4° C.; after washing with PBST, 10% of fetal calf serum was added and blocked at 37° C. for 1 hour; SS002M91, SG12473, SG12474 were diluted gradiently with 10% of fetal bovine blood respectively, and Biotin-Fc-CD47 was added into the samples until a final concentration of 2 μg/ml, and pre-incubated at 37° C. for 30 min, as the primary antibody; after the assay plate was washed with PBST, the primary antibody was added and incubated at 37° C. for 1 hour; after washing with PBST for 5 times, horseradish peroxidase-labeled avidin (Streptavidin-HRP, Jiaxuan Bio.) was added and incubated at 37° C. for 30 minutes; after washing with PBST for 5 times, each well was added with 100 μl TMB (eBioscience), and placed in dark at room temperature (20±5° C.) for 1-5 min; then each well was added with 100 μl 2N $H_2SO_4$ stop solution to terminate the reaction of the substrate, OD values were read at 450 nm on the microplate reader, and the blocking effects of SS002M91, SG12473, SG12474 on CD47/SIRPα were analyzed.

Figure 6:
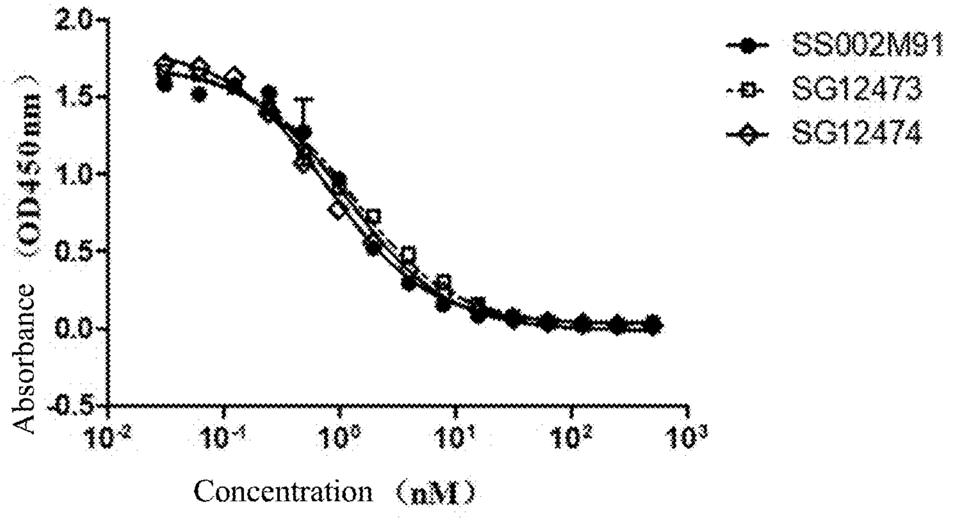
FIG. 6 shows that the fusion protein of the present application competitively blocks the binding between CD47 and its ligand SIRPα.

The results were shown in FIG. 6. FIG. 6 showed that the same as the fusion protein SS002M91, the fusion proteins SG12473, SG12474 could competitively block the binding between CD47 and its ligand SIRPα. Wherein, IC50 value of SG12473 was 1.26 nM, IC50 value of SG12474 was 0.77 nM, and IC50 value of SS002M91 was 1.16 nM.

Example 5 Analysis on the Activity of Blocking the PD-1/PD-L1 Interaction

With SG1201 and SG1202 as the control, the biological activities of the fusion proteins SG12473 and SG12474 to block the PD-1/PD-L1 interaction were evaluated.

PD-L1-Fc was coated on the assay plate at 2 ug/ml overnight at 4° C.; after washing with PBST, 10% of fetal calf serum was added and blocked at 37° C. for 1 hour; SG1201, SG12473, SG1202 and SG12474 were diluted gradiently with 10% of fetal bovine blood respectively, and Biotin-Fc-PD1 was added into the samples until a final concentration of 1 ug/ml, and pre-incubated at 37° C. for 30 min, as the primary antibody; after the assay plate was washed with PBST, the primary antibody was added and incubated at 37° C. for 1 hour; after washing with PBST for 5 times, horseradish peroxidase-labeled avidin (Streptavidin-HRP, Jiaxuan Bio.) was added and incubated at 37° C. for 30 minutes; after washing with PBST for 5 times, each well was added with 100 µl TMB (eBioscience), and placed in dark at room temperature (20±5° C.) for 1-5 min; then each well was added with 100 µl 2N $H_2SO_4$ stop solution to terminate the reaction of the substrate, OD values were read at 450 nm on the microplate reader, and the blocking effects of SG1201, SG12473, SG1202 and SG12474 on PD-1/PD-L1 were analyzed.

Figure 7:
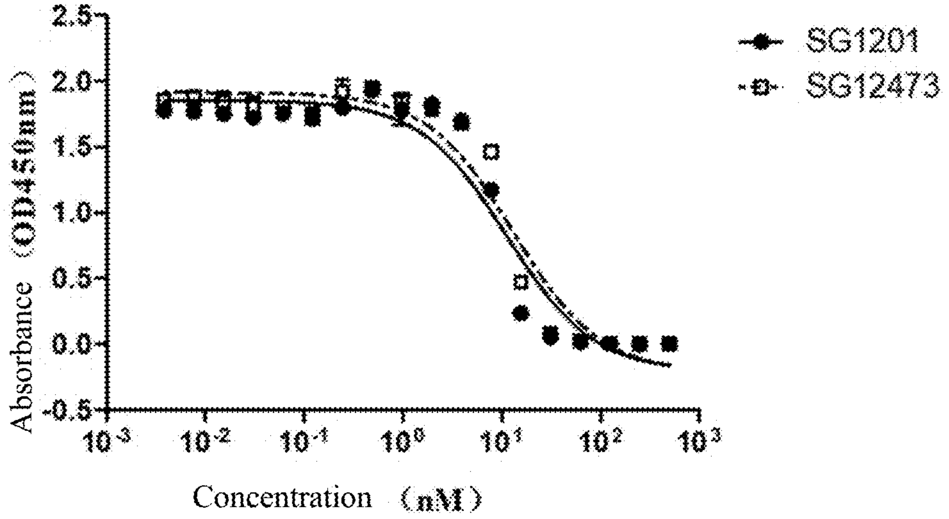
FIGS. 7-8 show that the fusion protein of the present application competitively blocks the binding between PD-1 and PD-L1.
Figure 8:
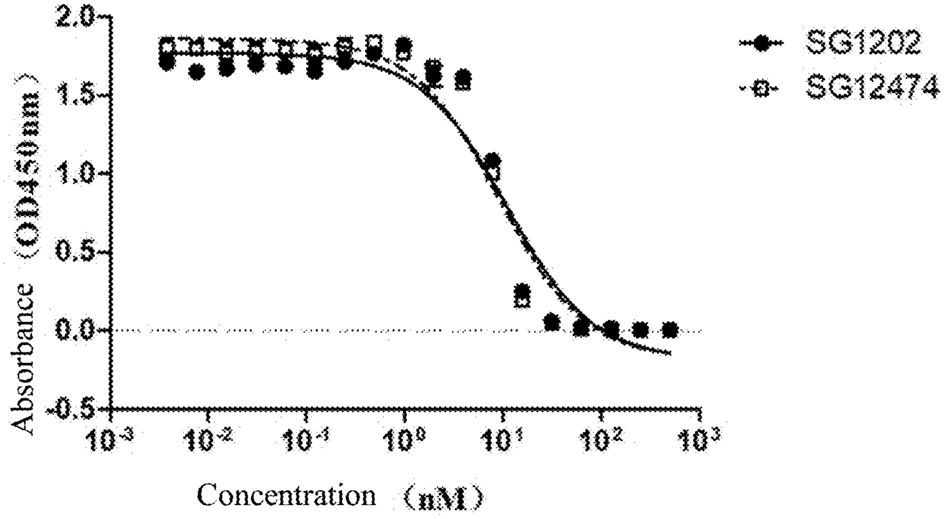

As can be seen from FIGS. 7-8, the same as SG1201 and SG1202, the fusion proteins SG12473 and SG12474 could competitively block the binding between PD-1 and PD-L1. Wherein, IC50 value of SG1201 is 11.23 nM, IC50 value of SG12473 is 13.22 nM, IC50 value of SG1202 is 10.89 nM, and IC50 value of SG12474 is 9.12 nM.

Example 6 Fusion Protein Inhibits the Tumor Activity In Vivo

A female NCG mouse MiXeno animal model was transplanted heterogeneously with a human-derived lymphoma KARPAS-299 cell line subcutaneously so as to evaluate the inhibitory effect of the fusion protein SG12473 on the tumor activity.

Female NCG mice of 6-8 weeks (purchased from Jiangsu Jicui Yaokang Biotechnology Co. Ltd.) were chosen for test. The mice were inoculated with KARPAS-299 cells subcutaneously and the growth profiles of tumors were observed periodically. When the tumors grew to an average size of 35 $mm^3$, the mice were randomly grouped according to the tumor size and the body weight of the mice for administration. At the day of grouping (about at Day 4), a fresh human PBMC (deriving from a donor) was inoculated through the tail vein so as to establish a KARPAS-299 humanized mouse model.

The tests were divided into a solvent control group, a SG1201 group as well as low, medium and high dosage groups of SG12473, in which there were 12 mice in each group and every 6 mice utilized PBMC from the same source. Drugs were given by intraperitoneal injection twice a week, for a period of totally three weeks. In particular, Group 1A and Group 1B: solvent control groups Group 2A and Group 2B: SG1201 groups, SG1201 at 5 mg/Kg Group 3A and Group 3B: low dosage groups of SG12473, SG12473 at 5 mg/Kg Group 4A and Group 4B: medium dosage groups of SG12473, SG12473 at 10 mg/Kg Group 5A and Group 5B: high dosage groups of SG12473, SG12473 at 20 mg/Kg;

The therapeutic efficacy was evaluated according to the relative tumor growth inhibition (TGI), and safety was evaluated based on the changes in animal weight and the death rate.

Figure 9:
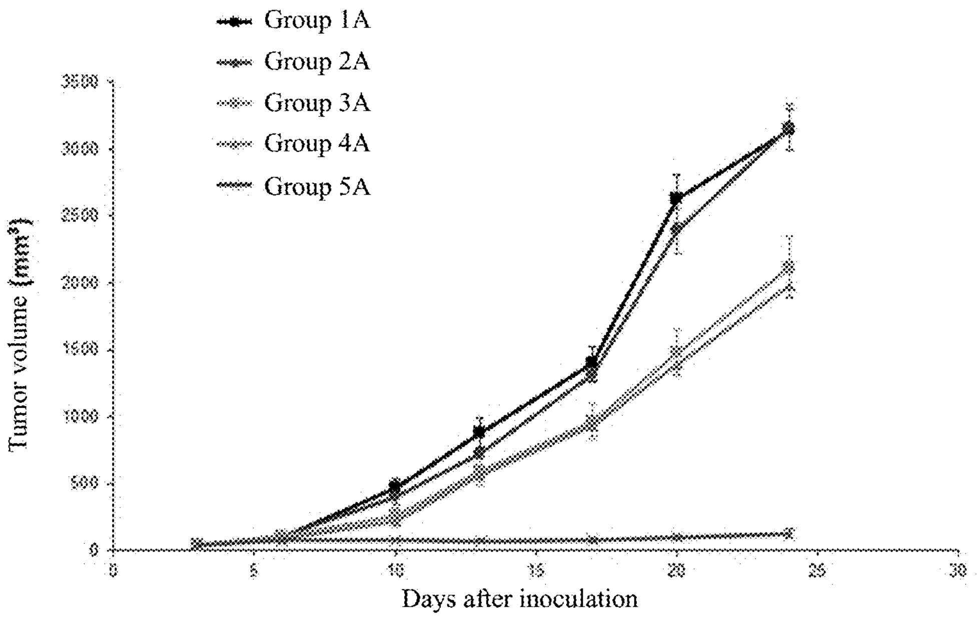
FIGS. 9-10 show that the growth of tumor volume in a mouse tumor model of human lymphoma is inhibited by use of the fusion protein of the present application.

The results showed that, in mice using PBMC derived from the donor A, significant tumor inhibitory effects were displayed in all the low, medium and high dosage groups of SG12473. As shown from the results in FIG. 9, TGI in the low, medium and high dosage groups of SG12473 at the completion of administration were 44.71%, 47.16% and 96.49% respectively; and 4 days after the completion of administration, TGI were 43.71%, 47.92% and 95.94% respectively, which had statistically significant difference relative to the solvent control groups (p values were all <0.01). No significant tumor inhibitory effect was displayed at the test dosage of SG1201.

Figure 10:
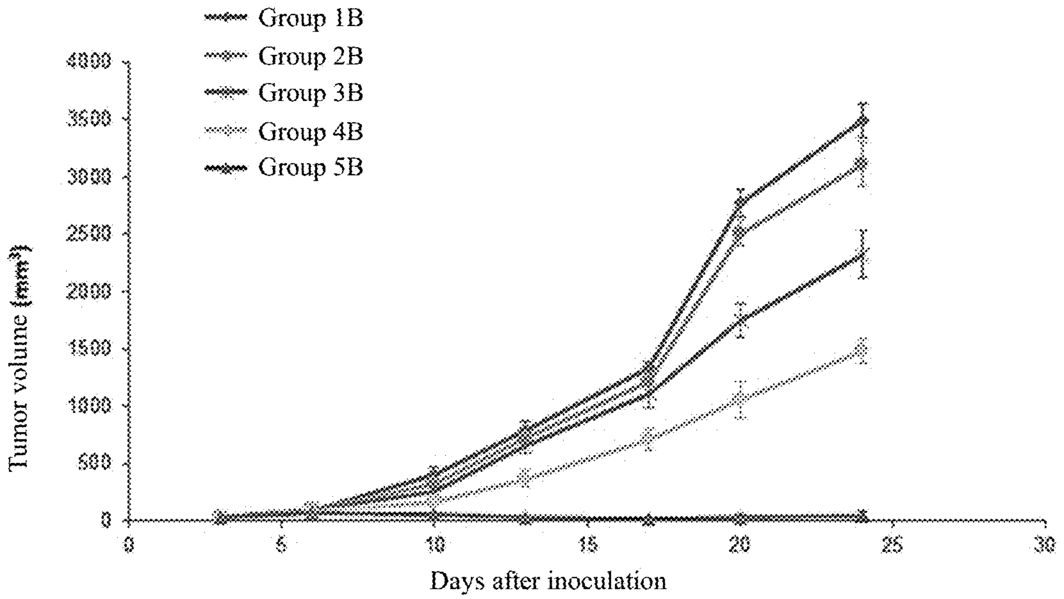

In mice using PBMC derived from the donor B, significant tumor inhibitory effects were displayed in all the low, medium and high dosage groups of SG12473. As shown from the results in FIG. 10, TGI in the low, medium and high dosage groups of SG12473 at the completion of administration were 36.96%, 62.06% and 98.90% respectively; and 4 days after the completion of administration, TGI were 33.44%, 57.57% and 98.83% respectively, which had statistically significant difference relative to the solvent control groups (p values were all <0.01). No significant tumor inhibitory effect was displayed at the test dosage of SG1201.

There were no animal deaths in each treatment group, no obvious drug toxicity was displayed, and the tolerance was good during the treatment.

The foregoing detailed description is provided by means of explanations and examples, but not intending to limit the scope of the attached claims. The various variations of the embodiments currently listed in the present application are apparent to those with ordinary skills in the art, and reserved within the scope of the attached claims and its equivalent schemes.

What is claimed is:

1. A fusion protein, comprising:

a first binding domain that specifically binds PD-L1; and a second binding domain that specifically binds a CD47 protein;

wherein, said second binding domain comprises a mutant of a human SIRPα variant 1, wherein said mutant of the human SIRPα variant 1 comprises an amino acid sequence as set forth in any one of SEQ ID NO:31, SEQ ID NO:32, SEQ ID NO:39, SEQ ID NO: 40, SEQ ID NO:41 and SEQ ID NO:43 and wherein said first binding domain comprises a PD-L1 antibody or an antigen-binding fragment thereof.

2. The fusion protein according to claim 1, wherein said PD-L1 antibody comprises a heavy chain and a light chain of the antibody or a fragment thereof, said heavy chain of the antibody or the fragment thereof comprises HCDR1-3 and said light chain of the antibody or the fragment thereof comprises LCDR1-3, said HCDR1-3 and LCDR1-3 comprise the amino acid sequence as shown in any one of the group consisting of:

(1) HCDR1: SEQ ID NO:4, HCDR2: SEQ ID NO:5, HCDR3: SEQ ID NO:6, LCDR1: SEQ ID NO:1, LCDR2: SEQ ID NO:2, LCDR3: SEQ ID NO:3; and (2) HCDR1: SEQ ID NO:18, HCDR2: SEQ ID NO:19, HCDR3: SEQ ID NO:20, LCDR1: SEQ ID NO:15, LCDR2: SEQ ID NO:16, LCDR3: SEQ ID NO:17.

3. The fusion protein according to claim 2, wherein said heavy chain of the antibody or the fragment thereof comprises a heavy chain variable region VH and said light chain of the antibody or the fragment thereof comprises a light chain variable region VL, and said heavy chain variable region VH and said light chain variable region VL comprise an amino acid sequence as shown in any one of the group consisting of:

(1) VH: SEQ ID NO:8, VL: SEQ ID NO:7; and (2) VH: SEQ ID NO:22, VL: SEQ ID NO:21.

4. The fusion protein according to claim 2, wherein said heavy chain and said light chain of the antibody comprise an amino acid sequence as shown in any one of the group consisting of:

(1) heavy chain: SEQ ID NO:13, light chain: SEQ ID NO:11; and (2) heavy chain: SEQ ID NO:27, light chain: SEQ ID NO:25.

5. The fusion protein according to claim 1, wherein said first binding domain is located at N-terminal of the second binding domain.

6. The fusion protein according to claim 1, wherein said fusion protein further comprises a linker, the linker is located at C-terminal of the first binding domain and located at N-terminal of the second binding domain, and wherein said linker comprises an amino acid sequence as shown in SEQ ID NO:52.

7. The fusion protein according to claim 1, comprising at least two of the second binding domain.

8. An immunoconjugate, comprising the fusion protein according to claim 1.

9. One or more isolated nucleic acid molecules, encoding the fusion protein according to claim 1.

10. One or more vectors, comprising the nucleic acid molecules according to claim 9.

11. A composition, comprising the fusion protein according to claim 1, and optionally, a pharmaceutically acceptable excipient.

12. A cell, comprising the fusion protein according to claim 1.

13. A method of preparing the fusion protein according to claim 1, comprising culturing the cell under a condition enabling the expression of said fusion protein.

14. A method of treating a tumor comprising administering to a subject in need thereof the fusion protein according to claim 1.

15. A method of blocking the interaction between PD-L1 protein and PD-1 or blocking the interaction between CD47 protein and SIRPα, comprising administering to a subject in need thereof an effective amount of the fusion protein according to claim 1.

16. A method of inhibiting the growth and/or proliferation of tumors or tumor cells, comprising administering to a subject in need thereof an effective amount of the fusion protein according to claim 1.

* * * * *

SEQUENCE LISTING

```
<160> NUMBER OF SEQ ID NOS: 55

<210> SEQ ID NO 1
<211> LENGTH: 11
<212> TYPE: PRT
<213> ORGANISM: Artificial Sequence
<220> FEATURE:
<223> OTHER INFORMATION: SG1201 LCDR1

<400> SEQUENCE: 1

Arg Ala Ser Gln Asp Val Ser Thr Ala Val Ala
1               5                   10


<210> SEQ ID NO 2
<211> LENGTH: 7
<212> TYPE: PRT
<213> ORGANISM: Artificial Sequence
<220> FEATURE:
<223> OTHER INFORMATION: SG1201 LCDR2
```

<400> SEQUENCE: 2

Ser Ala Ser Phe Leu Tyr Ser
1 5

<210> SEQ ID NO 3
<211> LENGTH: 9
<212> TYPE: PRT
<213> ORGANISM: Artificial Sequence
<220> FEATURE:
<223> OTHER INFORMATION: SG1201 LCDR3

<400> SEQUENCE: 3

Gln Gln Tyr Leu Tyr His Pro Ala Thr
1 5

<210> SEQ ID NO 4
<211> LENGTH: 5
<212> TYPE: PRT
<213> ORGANISM: Artificial Sequence
<220> FEATURE:
<223> OTHER INFORMATION: SG1201 HCDR1

<400> SEQUENCE: 4

Asp Ser Trp Ile His
1 5

<210> SEQ ID NO 5
<211> LENGTH: 17
<212> TYPE: PRT
<213> ORGANISM: Artificial Sequence
<220> FEATURE:
<223> OTHER INFORMATION: SG1201 HCDR2

<400> SEQUENCE: 5

Trp Ile Ser Pro Tyr Gly Gly Ser Thr Tyr Tyr Ala Asp Ser Val Lys
1 5 10 15

Gly

<210> SEQ ID NO 6
<211> LENGTH: 9
<212> TYPE: PRT
<213> ORGANISM: Artificial Sequence
<220> FEATURE:
<223> OTHER INFORMATION: SG1201 HCDR3

<400> SEQUENCE: 6

Arg His Trp Pro Gly Gly Phe Asp Tyr
1 5

<210> SEQ ID NO 7
<211> LENGTH: 107
<212> TYPE: PRT
<213> ORGANISM: Artificial Sequence
<220> FEATURE:
<223> OTHER INFORMATION: SG1201 VL

<400> SEQUENCE: 7

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

```
Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105


<210> SEQ ID NO 8
<211> LENGTH: 118
<212> TYPE: PRT
<213> ORGANISM: Artificial Sequence
<220> FEATURE:
<223> OTHER INFORMATION: SG1201 VH

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115


<210> SEQ ID NO 9
<211> LENGTH: 321
<212> TYPE: DNA
<213> ORGANISM: Artificial Sequence
<220> FEATURE:
<223> OTHER INFORMATION: SG1201 VL nucleotide

<400> SEQUENCE: 9

gacatccaga tgacccagag ccctagcagc ctgagcgcca gcgtgggcga cagggtgacc     60

atcacctgca gggccagcca ggacgtgagc accgccgtgg cctggtacca gcagaagcct    120

ggcaaggccc ctaagctgct gatctacagc gccagcttcc tgtacagcgg cgtgcctagc    180

aggttcagcg gcagcggcag cggcaccgac ttcaccctga ccatcagcag cctgcagcct    240

gaggacttcg ccacctacta ctgccagcag tacctgtacc accctgccac cttcggccag    300

ggcaccaagg tggagatcaa g                                              321


<210> SEQ ID NO 10
<211> LENGTH: 354
<212> TYPE: DNA
<213> ORGANISM: Artificial Sequence
<220> FEATURE:
<223> OTHER INFORMATION: SG1201 VH nucleotide

<400> SEQUENCE: 10

gaggtgcagc tggtggagag cggcggcggc ctggtgcagc ctggcggcag cctgaggctg     60
```

```
agctgcgccg ccagcggctt caccttcagc gacagctgga tccactgggt gaggcaggcc    120

cctggcaagg gcctggagtg ggtggcctgg atcagccctt acggcggcag cacctactac    180

gccgacagcg tgaagggcag gttcaccatc agcgccgaca ccagcaagaa caccgcctac    240

ctgcagatga acagcctgag ggccgaggac accgccgtgt actactgcgc caggaggcac    300

tggcctggcg gcttcgacta ctggggccag ggcaccctgg tgaccgtgag cagc          354


<210> SEQ ID NO 11
<211> LENGTH: 214
<212> TYPE: PRT
<213> ORGANISM: Artificial Sequence
<220> FEATURE:
<223> OTHER INFORMATION: SG1201 light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 645
<212> TYPE: DNA
<213> ORGANISM: Artificial Sequence
<220> FEATURE:
<223> OTHER INFORMATION: SG1201 light chain nucleotide

<400> SEQUENCE: 12

gacatccaga tgacccagag ccctagcagc ctgagcgcca gcgtgggcga cagggtgacc     60

atcacctgca gggccagcca ggacgtgagc accgccgtgg cctggtacca gcagaagcct    120

ggcaaggccc ctaagctgct gatctacagc gccagcttcc tgtacagcgg cgtgcctagc    180
```

-continued

```
aggttcagcg gcagcggcag cggcaccgac ttcaccctga ccatcagcag cctgcagcct    240

gaggacttcg ccacctacta ctgccagcag tacctgtacc accctgccac cttcggccag    300

ggcaccaagg tggagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

```
<210> SEQ ID NO 13
<211> LENGTH: 448
<212> TYPE: PRT
<213> ORGANISM: Artificial Sequence
<220> FEATURE:
<223> OTHER INFORMATION: SG1201 heavy chain

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 14
<211> LENGTH: 1344
<212> TYPE: DNA
<213> ORGANISM: Artificial Sequence
<220> FEATURE:
<223> OTHER INFORMATION: SG1201 heavy chain nucleotide

<400> SEQUENCE: 14
gaggtgcagc tggtggagag cggcggcggc ctggtgcagc ctggcggcag cctgaggctg 60
agctgcgccg ccagcggctt caccttcagc gacagctgga tccactgggt gaggcaggcc 120
cctggcaagg gcctggagtg ggtggcctgg atcagccctt acggcggcag cacctactac 180
gccgacagcg tgaagggcag gttcaccatc agcgccgaca ccagcaagaa caccgcctac 240
ctgcagatga acagcctgag ggccgaggac accgccgtgt actactgcgc caggaggcac 300
tggcctggcg gcttcgacta ctggggccag ggcaccctgg tgaccgtgag cagcgctagc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agaaagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acgtgcgtgg tggtggacgt gagccacgaa gaccccgagg tcaagttcaa ctggtacgtg 840
gacggcgtgg aggtgcataa tgccaagaca aagccgcggg aggagcagta cgccagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga agagatgacc 1080
aagaaccagg tcagcctgac ctgcctggtc aaaggcttct atcccagcga catcgccgtg 1140

```
gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344
```

<210> SEQ ID NO 15
<211> LENGTH: 12
<212> TYPE: PRT
<213> ORGANISM: Artificial Sequence
<220> FEATURE:
<223> OTHER INFORMATION: SG1202 LCDR1

<400> SEQUENCE: 15

```
Arg Ala Ser Gln Arg Val Ser Ser Ser Tyr Leu Ala
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: SG1202 LCDR2

<400> SEQUENCE: 16

```
Asp Ala Ser Ser Arg Ala Thr
1               5
```

<210> SEQ ID NO 17
<211> LENGTH: 9
<212> TYPE: PRT
<213> ORGANISM: Artificial Sequence
<220> FEATURE:
<223> OTHER INFORMATION: SG1202 LCDR3

<400> SEQUENCE: 17

```
Gln Gln Tyr Gly Ser Leu Pro Trp Thr
1               5
```

<210> SEQ ID NO 18
<211> LENGTH: 5
<212> TYPE: PRT
<213> ORGANISM: Artificial Sequence
<220> FEATURE:
<223> OTHER INFORMATION: SG1202 HCDR1

<400> SEQUENCE: 18

```
Arg Tyr Trp Met Ser
1               5
```

<210> SEQ ID NO 19
<211> LENGTH: 17
<212> TYPE: PRT
<213> ORGANISM: Artificial Sequence
<220> FEATURE:
<223> OTHER INFORMATION: SG1202 HCDR2

<400> SEQUENCE: 19

```
Asn Ile Lys Gln Asp Gly Ser Glu Lys Tyr Tyr Val Asp Ser Val Lys
1               5                   10                  15

Gly
```

<210> SEQ ID NO 20
<211> LENGTH: 12
<212> TYPE: PRT

<213> ORGANISM: Artificial Sequence
<220> FEATURE:
<223> OTHER INFORMATION: SG1202 HCDR3

<400> SEQUENCE: 20

```
Glu Gly Gly Trp Phe Gly Glu Leu Ala Phe Asp Tyr
1               5                   10
```

<210> SEQ ID NO 21
<211> LENGTH: 108
<212> TYPE: PRT
<213> ORGANISM: Artificial Sequence
<220> FEATURE:
<223> OTHER INFORMATION: SG1202 VL

<400> SEQUENCE: 21

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 22
<211> LENGTH: 121
<212> TYPE: PRT
<213> ORGANISM: Artificial Sequence
<220> FEATURE:
<223> OTHER INFORMATION: SG1202 VH

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

<210> SEQ ID NO 23
<211> LENGTH: 324
<212> TYPE: DNA
<213> ORGANISM: Artificial Sequence
<220> FEATURE:
<223> OTHER INFORMATION: SG1202 VL nucleotide

<400> SEQUENCE: 23
gagatcgtgc tgacccagtc ccctggcacc ctgtctctgt ctcccggcga gagagccacc 60
ctgtcttgcc gggcctccca gcgggtgtcc tcctcctacc tggcctggta tcagcagaaa 120
cccggacagg cccctaggct gctgatctac gacgcctcct ccagagccac cggcatccct 180
gaccggttct ccggctctgg ctccggcacc gacttcaccc tgaccatctc ccggctggaa 240
cctgaggact ttgccgtgta ttactgccag cagtacggct ccctgccttg gaccttcggc 300
cagggaacca aggtggagat caaa 324

<210> SEQ ID NO 24
<211> LENGTH: 363
<212> TYPE: DNA
<213> ORGANISM: Artificial Sequence
<220> FEATURE:
<223> OTHER INFORMATION: SG1202 VH nucleotide

<400> SEQUENCE: 24
gaggtgcagc tggtcgagtc tggcggagga ctggtgcagc ctggcggctc cctgagactg 60
tcttgcgccg cctccggctt caccttctcc cggtactgga tgtcttgggt gcgccaggct 120
cctggcaagg gactggaatg ggtggccaac atcaaacagg atggctctga gaagtactac 180
gtggactccg tgaagggccg gttcaccatc tccagggaca acgccaagaa ctccctgtac 240
ctgcagatga actccctgag ggccgaggac accgccgtgt actactgtgc ccgggagggc 300
ggatggttcg gcgagctggc cttcgattac tggggccagg gcaccctggt gacagtgtcc 360
tct 363

<210> SEQ ID NO 25
<211> LENGTH: 215
<212> TYPE: PRT
<213> ORGANISM: Artificial Sequence
<220> FEATURE:
<223> OTHER INFORMATION: SG1202 light chain

<400> SEQUENCE: 25

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser

```
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 26
<211> LENGTH: 648
<212> TYPE: DNA
<213> ORGANISM: Artificial Sequence
<220> FEATURE:
<223> OTHER INFORMATION: SG1202 light chain nucleotide

<400> SEQUENCE: 26

gagatcgtgc tgacccagtc ccctggcacc ctgtctctgt ctcccggcga gagagccacc     60

ctgtcttgcc gggcctccca gcgggtgtcc tcctcctacc tggcctggta tcagcagaaa    120

cccggacagg cccctaggct gctgatctac gacgcctcct ccagagccac cggcatccct    180

gaccggttct ccggctctgg ctccggcacc gacttcaccc tgaccatctc ccggctggaa    240

cctgaggact ttgccgtgta ttactgccag cagtacggct ccctgccttg gaccttcggc    300

cagggaacca aggtggagat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648


<210> SEQ ID NO 27
<211> LENGTH: 451
<212> TYPE: PRT
<213> ORGANISM: Artificial Sequence
<220> FEATURE:
<223> OTHER INFORMATION: SG1202 heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 28
<211> LENGTH: 1353
<212> TYPE: DNA
<213> ORGANISM: Artificial Sequence
<220> FEATURE:
<223> OTHER INFORMATION: SG1202 heavy chain nucleotide

<400> SEQUENCE: 28

```
gaggtgcagc tggtcgagtc tggcggagga ctggtgcagc ctggcggctc cctgagactg      60

tcttgcgccg cctccggctt caccttctcc cggtactgga tgtcttgggt gcgccaggct     120

cctggcaagg gactggaatg ggtggccaac atcaaacagg atggctctga gaagtactac     180
```

```
gtggactccg tgaagggccg gttcaccatc tccagggaca acgccaagaa ctccctgtac    240

ctgcagatga actccctgag ggccgaggac accgccgtgt actactgtgc ccgggagggc    300

ggatggttcg gcgagctggc cttcgattac tggggccagg gcaccctggt gacagtgtcc    360

tctgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca cgtgcgtggt ggtggacgtg agccacgaag accccgaggt caagttcaac    840

tggtacgtgg acggcgtgga ggtgcataat gccaagacaa agccgcggga ggagcagtac    900

gccagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggaa   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353


<210> SEQ ID NO 29
<211> LENGTH: 117
<212> TYPE: PRT
<213> ORGANISM: Homo sapiens

<400> SEQUENCE: 29

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115


<210> SEQ ID NO 30
<211> LENGTH: 117
<212> TYPE: PRT
<213> ORGANISM: Artificial Sequence
<220> FEATURE:
```

<223> OTHER INFORMATION: M1

<400> SEQUENCE: 30

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Ile Gly
20 25 30

Pro Ile Gln Trp Phe Arg Gly Ala Gly Pro Gly Arg Ile Leu Ile Tyr
35 40 45

Asn Gln Lys Lys Gly His Phe Pro Arg Val Thr Thr Leu Ser Asp Ser
50 55 60

Thr Arg Arg Gly Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Leu Glu Phe Lys Ser Gly Ala Gly Thr Glu Leu Ser Val
100 105 110

Arg Ala Lys Pro Ser
115

<210> SEQ ID NO 31
<211> LENGTH: 117
<212> TYPE: PRT
<213> ORGANISM: Artificial Sequence
<220> FEATURE:
<223> OTHER INFORMATION: M5

<400> SEQUENCE: 31

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Val Pro Val Gly
20 25 30

Pro Ile Gln Trp Phe Arg Gly Ala Gly Pro Gly Arg Asn Leu Ile Tyr
35 40 45

Asn Ser Arg His Gly His Phe Pro Arg Val Thr Thr Val Ser Asp Leu
50 55 60

Thr Lys Arg Asn Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Val Glu Phe Lys Ser Gly Ala Gly Thr Glu Leu Ser Val
100 105 110

Arg Ala Lys Pro Ser
115

<210> SEQ ID NO 32
<211> LENGTH: 117
<212> TYPE: PRT
<213> ORGANISM: Artificial Sequence
<220> FEATURE:
<223> OTHER INFORMATION: M12

<400> SEQUENCE: 32

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Phe Pro Ile Gly
20 25 30

Pro Ile Gln Trp Phe Arg Gly Ala Gly Pro Gly Arg Glu Leu Ile Tyr

```
        35                  40                  45

Asn Gln Arg Lys Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115


<210> SEQ ID NO 33
<211> LENGTH: 117
<212> TYPE: PRT
<213> ORGANISM: Artificial Sequence
<220> FEATURE:
<223> OTHER INFORMATION: M35

<400> SEQUENCE: 33

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Val Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115


<210> SEQ ID NO 34
<211> LENGTH: 117
<212> TYPE: PRT
<213> ORGANISM: Artificial Sequence
<220> FEATURE:
<223> OTHER INFORMATION: M37

<400> SEQUENCE: 34

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Lys Leu Ile Tyr
        35                  40                  45

Asn Gln Arg Asp Gly His Phe Pro Arg Val Thr Thr Val Ser Asp Leu
    50                  55                  60

Thr Lys Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95
```

Pro Asp Asp Val Glu Phe Lys Ser Gly Ala Gly Thr Glu Leu Ser Val
100 105 110

Arg Ala Lys Pro Ser
115

<210> SEQ ID NO 35
<211> LENGTH: 117
<212> TYPE: PRT
<213> ORGANISM: Artificial Sequence
<220> FEATURE:
<223> OTHER INFORMATION: M41

<400> SEQUENCE: 35

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Val Pro Val Gly
20 25 30

Pro Ile Gln Trp Phe Arg Gly Ala Gly Pro Gly Arg His Leu Ile Tyr
35 40 45

Asn Arg Arg His Gly His Phe Pro Arg Val Thr Thr Val Ser Asp Leu
50 55 60

Thr Lys Arg Asn Asn Met Asp Phe Ser Ile Ser Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Val Glu Phe Lys Ser Gly Ala Gly Thr Glu Leu Ser Val
100 105 110

Arg Ala Lys Pro Ser
115

<210> SEQ ID NO 36
<211> LENGTH: 117
<212> TYPE: PRT
<213> ORGANISM: Artificial Sequence
<220> FEATURE:
<223> OTHER INFORMATION: M57

<400> SEQUENCE: 36

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Val Gly
20 25 30

Pro Ile Gln Trp Phe Arg Gly Ala Gly Pro Gly Arg Ile Leu Ile Tyr
35 40 45

Asn Gly Lys Arg Gly His Phe Pro Arg Val Thr Thr Leu Ser Asp Thr
50 55 60

Thr Lys Arg Gly Asn Met Asp Phe Ser Ile Ser Ile Arg Asn Ile Thr
65 70 75 80

Pro Ala Asp Ala Gly Thr Tyr Tyr Cys Val Lys Phe Arg Lys Gly Ser
85 90 95

Pro Asp Asp Arg Glu Phe Lys Ser Gly Ala Gly Thr Glu Leu Ser Val
100 105 110

Arg Ala Lys Pro Ser
115

<210> SEQ ID NO 37
<211> LENGTH: 117
<212> TYPE: PRT
<213> ORGANISM: Artificial Sequence

<220> FEATURE:
<223> OTHER INFORMATION: M67

<400> SEQUENCE: 37

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Val Gly
20 25 30

Pro Ile Gln Trp Phe Arg Gly Ala Gly Pro Gly Arg Met Leu Ile Tyr
35 40 45

Asn Gly Arg Asp Gly His Phe Pro Arg Val Thr Thr Val Ser Asp Leu
50 55 60

Thr Lys Arg Asn Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Leu Glu Phe Lys Ser Gly Ala Gly Thr Glu Leu Ser Val
100 105 110

Arg Ala Lys Pro Ser
115

<210> SEQ ID NO 38
<211> LENGTH: 117
<212> TYPE: PRT
<213> ORGANISM: Artificial Sequence
<220> FEATURE:
<223> OTHER INFORMATION: M81

<400> SEQUENCE: 38

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Val Gly
20 25 30

Pro Ile Gln Trp Phe Arg Gly Ala Gly Pro Gly Arg Glu Leu Ile Tyr
35 40 45

Asn Gln Lys Glu Gly His Phe Pro Arg Val Thr Thr Val Ser Asp Leu
50 55 60

Thr Lys Arg Asn Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Val Glu Phe Lys Ser Gly Ala Gly Thr Glu Leu Ser Val
100 105 110

Arg Ala Lys Pro Ser
115

<210> SEQ ID NO 39
<211> LENGTH: 117
<212> TYPE: PRT
<213> ORGANISM: Artificial Sequence
<220> FEATURE:
<223> OTHER INFORMATION: M82

<400> SEQUENCE: 39

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Phe Pro Val Gly
20 25 30

```
Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Lys Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser
        115


<210> SEQ ID NO 40
<211> LENGTH: 117
<212> TYPE: PRT
<213> ORGANISM: Artificial Sequence
<220> FEATURE:
<223> OTHER INFORMATION: M84

<400> SEQUENCE: 40

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Arg Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser
        115


<210> SEQ ID NO 41
<211> LENGTH: 117
<212> TYPE: PRT
<213> ORGANISM: Artificial Sequence
<220> FEATURE:
<223> OTHER INFORMATION: M91

<400> SEQUENCE: 41

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Ala Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95
```

Pro Asp Asp Ile Glu Phe Lys Ser Gly Ala Gly Thr Glu Leu Ser Val
100 105 110

Arg Ala Lys Pro Ser
115

<210> SEQ ID NO 42
<211> LENGTH: 117
<212> TYPE: PRT
<213> ORGANISM: Artificial Sequence
<220> FEATURE:
<223> OTHER INFORMATION: M99

<400> SEQUENCE: 42

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Ile Pro Val Gly
20 25 30

Pro Ile Gln Trp Phe Arg Gly Ala Gly Pro Gly Arg Lys Leu Ile Tyr
35 40 45

Asn Gln Lys Glu Gly His Phe Pro Arg Val Thr Thr Val Ser Asp Ser
50 55 60

Thr Lys Arg Lys Asn Met Asp Phe Ser Ile Arg Ile His Asn Ile Thr
65 70 75 80

Pro Ala Asp Ala Gly Thr Tyr Tyr Cys Val Lys Phe Arg Lys Gly Ser
85 90 95

Pro Asp Asp Leu Glu Phe Lys Ser Gly Ala Gly Thr Glu Leu Ser Val
100 105 110

Arg Ala Lys Pro Ser
115

<210> SEQ ID NO 43
<211> LENGTH: 117
<212> TYPE: PRT
<213> ORGANISM: Artificial Sequence
<220> FEATURE:
<223> OTHER INFORMATION: M102

<400> SEQUENCE: 43

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Ile Gly
20 25 30

Pro Ile Gln Trp Phe Arg Gly Ala Gly Pro Gly Arg Glu Leu Ile Tyr
35 40 45

Asn Gly Lys Gly Gly His Phe Pro Arg Val Thr Thr Val Ser Arg Ser
50 55 60

Thr Lys Arg Asp Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Ile Glu Phe Lys Ser Gly Ala Gly Thr Glu Leu Ser Val
100 105 110

Arg Ala Lys Pro Ser
115

<210> SEQ ID NO 44
<211> LENGTH: 117
<212> TYPE: PRT

<213> ORGANISM: Artificial Sequence
<220> FEATURE:
<223> OTHER INFORMATION: M111

<400> SEQUENCE: 44

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Arg Leu Ile Tyr
        35                  40                  45

Asn Asn Arg Gly Gly His Phe Pro Arg Val Thr Thr Leu Ser Glu Thr
    50                  55                  60

Thr Arg Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
        115
```

<210> SEQ ID NO 45
<211> LENGTH: 117
<212> TYPE: PRT
<213> ORGANISM: Artificial Sequence
<220> FEATURE:
<223> OTHER INFORMATION: M122

<400> SEQUENCE: 45

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Asn Leu Ile Tyr
        35                  40                  45

Asn Ser Arg His Gly His Phe Pro Arg Val Thr Thr Ala Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115
```

<210> SEQ ID NO 46
<211> LENGTH: 117
<212> TYPE: PRT
<213> ORGANISM: Artificial Sequence
<220> FEATURE:
<223> OTHER INFORMATION: M126

<400> SEQUENCE: 46

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Ile Gly
            20                  25                  30
```

Pro Ile Gln Trp Phe Arg Gly Ala Gly Pro Gly Arg Val Leu Ile Tyr
35 40 45

Asn Gln Arg Asp Gly His Phe Pro Arg Val Thr Thr Val Ser Glu Thr
50 55 60

Thr Arg Arg Glu Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Val Glu Phe Lys Ser Gly Ala Gly Thr Glu Leu Ser Val
100 105 110

Arg Ala Lys Pro Ser
115

<210> SEQ ID NO 47
<211> LENGTH: 117
<212> TYPE: PRT
<213> ORGANISM: Artificial Sequence
<220> FEATURE:
<223> OTHER INFORMATION: M130

<400> SEQUENCE: 47

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Ile Gly
20 25 30

Pro Ile Gln Trp Phe Arg Gly Ala Gly Pro Gly Arg Val Leu Ile Tyr
35 40 45

Asn Gln Arg Glu Gly His Phe Pro Arg Val Thr Thr Val Ser Glu Ser
50 55 60

Thr Arg Arg Asp Asn Met Asp Phe Ser Ile Arg Ile Arg Asn Ile Thr
65 70 75 80

Pro Ala Asp Ala Gly Thr Tyr Tyr Cys Val Lys Phe Arg Lys Gly Ser
85 90 95

Pro Asp Asp Val Glu Phe Lys Ser Gly Ala Gly Thr Glu Leu Ser Val
100 105 110

Arg Ala Lys Pro Ser
115

<210> SEQ ID NO 48
<211> LENGTH: 117
<212> TYPE: PRT
<213> ORGANISM: Artificial Sequence
<220> FEATURE:
<223> OTHER INFORMATION: M135

<400> SEQUENCE: 48

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Val Pro Val Gly
20 25 30

Pro Ile Gln Trp Phe Arg Gly Ala Gly Pro Gly Arg Leu Leu Ile Tyr
35 40 45

Asn Gly Lys Gly Gly His Phe Pro Arg Val Thr Thr Leu Ser Glu Thr
50 55 60

Thr Arg Arg Gly Asn Met Asp Phe Ser Ile Arg Ile Gly Asn Ile Thr
65 70 75 80

Pro Ala Asp Ala Gly Thr Tyr Tyr Cys Val Lys Phe Arg Lys Gly Ser

```
                85                  90                  95

Pro Asp Asp Val Glu Phe Lys Ser Gly Ala Gly Thr Glu Leu Ser Val
            100                 105                 110

Arg Ala Lys Pro Ser
        115


<210> SEQ ID NO 49
<211> LENGTH: 117
<212> TYPE: PRT
<213> ORGANISM: Artificial Sequence
<220> FEATURE:
<223> OTHER INFORMATION: M145

<400> SEQUENCE: 49

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Asn Leu Ile Tyr
        35                  40                  45

Asn Gly Lys Gly Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115


<210> SEQ ID NO 50
<211> LENGTH: 233
<212> TYPE: PRT
<213> ORGANISM: Artificial Sequence
<220> FEATURE:
<223> OTHER INFORMATION: IgG1-FC

<400> SEQUENCE: 50

Leu Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140
```

```
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 51
<211> LENGTH: 232
<212> TYPE: PRT
<213> ORGANISM: Artificial Sequence
<220> FEATURE:
<223> OTHER INFORMATION: Mutant FC

<400> SEQUENCE: 51

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 52
<211> LENGTH: 10
<212> TYPE: PRT
<213> ORGANISM: Artificial Sequence
<220> FEATURE:
```

<223> OTHER INFORMATION: linker 1

<400> SEQUENCE: 52

Gly Gly Gly Gly Ser Gly Gly Gly Gly Ser
1 5 10

<210> SEQ ID NO 53
<211> LENGTH: 575
<212> TYPE: PRT
<213> ORGANISM: Artificial Sequence
<220> FEATURE:
<223> OTHER INFORMATION: SG12473 second polypeptide chain

<400> SEQUENCE: 53

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Ala Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Glu Leu Gln Val Ile Gln
    450                 455                 460

Pro Asp Lys Ser Val Leu Val Ala Ala Gly Glu Thr Ala Thr Leu Arg
465                 470                 475                 480

Cys Thr Ala Thr Ser Leu Leu Pro Val Gly Pro Ile Gln Trp Phe Arg
                485                 490                 495

Gly Ala Gly Pro Gly Arg Gln Leu Ile Tyr Asn Gln Lys Asp Gly His
            500                 505                 510

Phe Pro Arg Val Thr Thr Ala Ser Asp Leu Thr Lys Arg Asn Asn Met
        515                 520                 525

Asp Phe Ser Ile Asn Ile Gly Asn Ile Thr Pro Ala Asp Ala Gly Thr
    530                 535                 540

Tyr Tyr Cys Val Lys Phe Arg Lys Gly Ser Pro Asp Asp Ile Glu Phe
545                 550                 555                 560

Lys Ser Gly Ala Gly Thr Glu Leu Ser Val Arg Ala Lys Pro Ser
                565                 570                 575


<210> SEQ ID NO 54
<211> LENGTH: 578
<212> TYPE: PRT
<213> ORGANISM: Artificial Sequence
<220> FEATURE:
<223> OTHER INFORMATION: SG12474 second polypeptide chain

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125
```

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Glu Leu Gln
    450                 455                 460

Val Ile Gln Pro Asp Lys Ser Val Leu Val Ala Ala Gly Glu Thr Ala
465                 470                 475                 480

Thr Leu Arg Cys Thr Ala Thr Ser Leu Leu Pro Val Gly Pro Ile Gln
                485                 490                 495

Trp Phe Arg Gly Ala Gly Pro Gly Arg Gln Leu Ile Tyr Asn Gln Lys
            500                 505                 510

Asp Gly His Phe Pro Arg Val Thr Thr Ala Ser Asp Leu Thr Lys Arg
        515                 520                 525

Asn Asn Met Asp Phe Ser Ile Asn Ile Gly Asn Ile Thr Pro Ala Asp
    530                 535                 540
```

Ala Gly Thr Tyr Tyr Cys Val Lys Phe Arg Lys Gly Ser Pro Asp Asp
545 550 555 560

Ile Glu Phe Lys Ser Gly Ala Gly Thr Glu Leu Ser Val Arg Ala Lys
565 570 575

Pro Ser

<210> SEQ ID NO 55
<211> LENGTH: 350
<212> TYPE: PRT
<213> ORGANISM: Artificial Sequence
<220> FEATURE:
<223> OTHER INFORMATION: SS002M91 monomer

<400> SEQUENCE: 55

Glu Leu Gln Val Ile Gln Pro Asp Lys Ser Val Leu Val Ala Ala Gly
1 5 10 15

Glu Thr Ala Thr Leu Arg Cys Thr Ala Thr Ser Leu Leu Pro Val Gly
20 25 30

Pro Ile Gln Trp Phe Arg Gly Ala Gly Pro Gly Arg Gln Leu Ile Tyr
35 40 45

Asn Gln Lys Asp Gly His Phe Pro Arg Val Thr Thr Ala Ser Asp Leu
50 55 60

Thr Lys Arg Asn Asn Met Asp Phe Ser Ile Asn Ile Gly Asn Ile Thr
65 70 75 80

Pro Ala Asp Ala Gly Thr Tyr Tyr Cys Val Lys Phe Arg Lys Gly Ser
85 90 95

Pro Asp Asp Ile Glu Phe Lys Ser Gly Ala Gly Thr Glu Leu Ser Val
100 105 110

Arg Ala Lys Pro Ser Leu Glu Pro Lys Ser Cys Asp Lys Thr His Thr
115 120 125

Cys Pro Pro Cys Pro Ala Pro Glu Leu Leu Gly Gly Pro Ser Val Phe
130 135 140

Leu Phe Pro Pro Lys Pro Lys Asp Thr Leu Met Ile Ser Arg Thr Pro
145 150 155 160

Glu Val Thr Cys Val Val Val Asp Val Ser His Glu Asp Pro Glu Val
165 170 175

Lys Phe Asn Trp Tyr Val Asp Gly Val Glu Val His Asn Ala Lys Thr
180 185 190

Lys Pro Arg Glu Glu Gln Tyr Asn Ser Thr Tyr Arg Val Val Ser Val
195 200 205

Leu Thr Val Leu His Gln Asp Trp Leu Asn Gly Lys Glu Tyr Lys Cys
210 215 220

Lys Val Ser Asn Lys Ala Leu Pro Ala Pro Ile Glu Lys Thr Ile Ser
225 230 235 240

Lys Ala Lys Gly Gln Pro Arg Glu Pro Gln Val Tyr Thr Leu Pro Pro
245 250 255

Ser Arg Asp Glu Leu Thr Lys Asn Gln Val Ser Leu Thr Cys Leu Val
260 265 270

Lys Gly Phe Tyr Pro Ser Asp Ile Ala Val Glu Trp Glu Ser Asn Gly
275 280 285

Gln Pro Glu Asn Asn Tyr Lys Thr Thr Pro Pro Val Leu Asp Ser Asp
290 295 300

Gly Ser Phe Phe Leu Tyr Ser Lys Leu Thr Val Asp Lys Ser Arg Trp
305 310 315 320

-continued

```
Gln Gln Gly Asn Val Phe Ser Cys Ser Val Met His Glu Ala Leu His
            325                 330                 335

Asn His Tyr Thr Gln Lys Ser Leu Ser Leu Ser Pro Gly Lys
        340                 345                 350
```